(12) United States Patent
Chmait et al.

(10) Patent No.: US 11,763,277 B2
(45) Date of Patent: *Sep. 19, 2023

(54) SYSTEMS AND METHODS FOR A HEALTH CARE E-COMMERCE MARKETPLACE

(71) Applicant: Cambia Health Solutions, Inc., Portland, OR (US)

(72) Inventors: Marcee Chmait, North Hills, CA (US); Christopher Coogan, Portland, OR (US); Elizabeth Anne Berselli, Portland, OR (US); Will Cooper, Berkeley, CA (US)

(73) Assignee: Cambia Health Solutions, Inc., Portland, OR (US)

( * ) Notice: Subject to any disclaimer, the term of this patent is extended or adjusted under 35 U.S.C. 154(b) by 551 days.

This patent is subject to a terminal disclaimer.

(21) Appl. No.: 16/890,956

(22) Filed: Jun. 2, 2020

(65) Prior Publication Data

US 2020/0365259 A1 Nov. 19, 2020

Related U.S. Application Data

(62) Division of application No. 14/845,170, filed on Sep. 3, 2015, now Pat. No. 10,706,963.

(Continued)

(51) Int. Cl.
*G06Q 20/10* (2012.01)
*G06Q 30/0601* (2023.01)
(Continued)

(52) U.S. Cl.
CPC ......... *G06Q 20/102* (2013.01); *G06Q 10/10* (2013.01); *G06Q 20/14* (2013.01);
(Continued)

(58) Field of Classification Search
CPC ...... G06Q 20/102; G06Q 10/10; G06Q 20/14; G06Q 30/0633; G06Q 40/08; G16H 40/20
See application file for complete search history.

(56) References Cited

U.S. PATENT DOCUMENTS 5,359,509 A 10/1994 Little et al.
5,544,044 A 8/1996 Leatherman
(Continued)

FOREIGN PATENT DOCUMENTS

WO WO-2013049854 A1 * 4/2013 ........... G06F 19/322

OTHER PUBLICATIONS

Chao et al., Billing for physician services: a comparison of actual billing with CPT codes assigned by direct observation, Jul. 1998, Journal of Family Practice, pp. 28-32. (Year: 1998).*

*Primary Examiner* — Christopher L Gilligan
(74) *Attorney, Agent, or Firm* — McCoy Russell LLP

(57) ABSTRACT

Systems and methods for an e-commerce health care marketplace are provided. In one embodiment, a method comprises, responsive to a query from a user, retrieving from a database a list of responses comprising one or more health care providers offering one or more health care services at a provider-supplied price; filtering the list of responses based on a geographic location included in the query; providing, for display, the filtered list of responses; receiving a payment from the user for a response selected from the filtered list of responses; automatically sending a notification of the payment to a provider associated with the selected response; and responsive to receiving an order fulfillment notification from the provider, automatically providing the payment to the provider. In this way, health care consumers may make informed purchasing decisions when shopping for health (Continued)

care services and health care providers may receive prompt payment for services delivered.

14 Claims, 30 Drawing Sheets

Related U.S. Application Data

(60) Provisional application No. 62/048,157, filed on Sep. 9, 2014.

(51) Int. Cl.
*G06Q 20/14* (2012.01)
*G16H 40/20* (2018.01)
*G06Q 10/10* (2023.01)
*G06Q 40/08* (2012.01)

(52) U.S. Cl.
CPC ......... *G06Q 30/0633* (2013.01); *G06Q 40/08* (2013.01); *G16H 40/20* (2018.01); *Y02A 90/10* (2018.01)

(56) References Cited

U.S. PATENT DOCUMENTS

| | | | |
|---|---|---|---|
| 6,112,183 A | 8/2000 | Swanson et al. | |
| 6,208,973 B1 | 3/2001 | Boyer et al. | |
| 6,311,170 B1 | 10/2001 | Embrey | |
| 6,735,569 B1 | 5/2004 | Wizig | |
| 7,213,750 B1 | 5/2007 | Barnes et al. | |
| 7,346,522 B1 | 3/2008 | Baylor et al. | |
| 7,624,026 B2 | 11/2009 | DiPiero et al. | |
| 7,630,937 B1 | 12/2009 | Mo et al. | |
| 7,693,728 B2 | 4/2010 | Underwood et al. | |
| 7,702,530 B2 | 4/2010 | Pearson | |
| 7,873,528 B2 | 1/2011 | Bregante et al. | |
| 7,925,518 B2 | 4/2011 | Lee et al. | |
| 8,214,230 B1 | 7/2012 | DiPiero et al. | |
| 8,428,963 B2 | 4/2013 | Underwood et al. | |
| 8,484,112 B2 | 7/2013 | Bissoon et al. | |
| 8,498,885 B2 | 7/2013 | Vanderzee et al. | |
| 8,510,124 B2 | 8/2013 | Gowdy et al. | |
| 8,538,875 B2 | 9/2013 | Seib et al. | |
| 8,626,536 B2 | 1/2014 | Davis et al. | |
| 8,645,162 B2 | 2/2014 | Boerger et al. | |
| 8,670,993 B2 | 3/2014 | Henley | |
| 8,682,688 B1 | 3/2014 | Coluni et al. | |
| 8,700,427 B1 | 4/2014 | Parks et al. | |
| 8,706,524 B2 | 4/2014 | DiPiero et al. | |
| 8,712,797 B1 | 4/2014 | Bezdek et al. | |
| 8,731,962 B2 | 5/2014 | Seib et al. | |
| 9,123,072 B2 | 9/2015 | Ketchel, III | |
| 2002/0087444 A1 | 7/2002 | DiPiero et al. | |
| 2002/0111916 A1 | 8/2002 | Coronna et al. | |
| 2002/0147678 A1 | 10/2002 | Drunsic | |
| 2004/0236605 A1 | 11/2004 | Somani | |
| 2006/0106640 A1 | 5/2006 | Deline | |
| 2006/0136264 A1 | 6/2006 | Eaton et al. | |
| 2007/0106607 A1 | 5/2007 | Seib et al. | |
| 2007/0168234 A1 | 7/2007 | Rutkowski et al. | |
| 2008/0288286 A1 | 11/2008 | Noreen et al. | |
| 2009/0094055 A1* | 4/2009 | Gage, Jr | G16H 10/60 705/400 |
| 2009/0125348 A1 | 5/2009 | Rastogi | |
| 2009/0144088 A1 | 6/2009 | Zubiller et al. | |
| 2009/0313076 A1 | 12/2009 | Schoenberg | |
| 2010/0185466 A1* | 7/2010 | Paradis | G06Q 20/347 705/4 |
| 2011/0004486 A1 | 1/2011 | Smith | |
| 2011/0071854 A1 | 3/2011 | Medeiros et al. | |
| 2012/0054119 A1 | 3/2012 | Zecchini | |
| 2012/0232936 A1 | 9/2012 | Bravata et al. | |
| 2012/0253830 A1 | 10/2012 | John et al. | |
| 2012/0259654 A1 | 10/2012 | Vanderzee et al. | |
| 2012/0296815 A1 | 11/2012 | Seib et al. | |
| 2013/0204634 A1 | 8/2013 | Kiridena | |
| 2013/0246090 A1 | 9/2013 | Hoffman et al. | |
| 2013/0246091 A1 | 9/2013 | Underwood et al. | |
| 2013/0332199 A1 | 12/2013 | Freiwat et al. | |
| 2014/0074500 A1 | 3/2014 | Seib et al. | |
| 2014/0088986 A1 | 3/2014 | Gowdy et al. | |
| 2014/0088999 A1 | 3/2014 | Davis et al. | |
| 2014/0095195 A1 | 4/2014 | Davis et al. | |
| 2014/0122108 A1 | 5/2014 | Malven et al. | |
| 2014/0142964 A1 | 5/2014 | Lang et al. | |
| 2014/0142973 A1 | 5/2014 | Henley | |
| 2014/0149135 A1 | 5/2014 | Boerger et al. | |
| 2014/0244546 A1 | 8/2014 | Bezdek et al. | |
| 2014/0372134 A1 | 12/2014 | Dahr | |
| 2014/0372147 A1 | 12/2014 | White | |
| 2015/0052009 A1* | 2/2015 | Ketchell, III | G06Q 20/065 705/26.8 |
| 2015/0294338 A1 | 10/2015 | Ketchel, III et al. | |
| 2015/0356663 A1 | 12/2015 | Ketchel, III et al. | |
| 2016/0027085 A1 | 1/2016 | Ketchel, III et al. | |

* cited by examiner

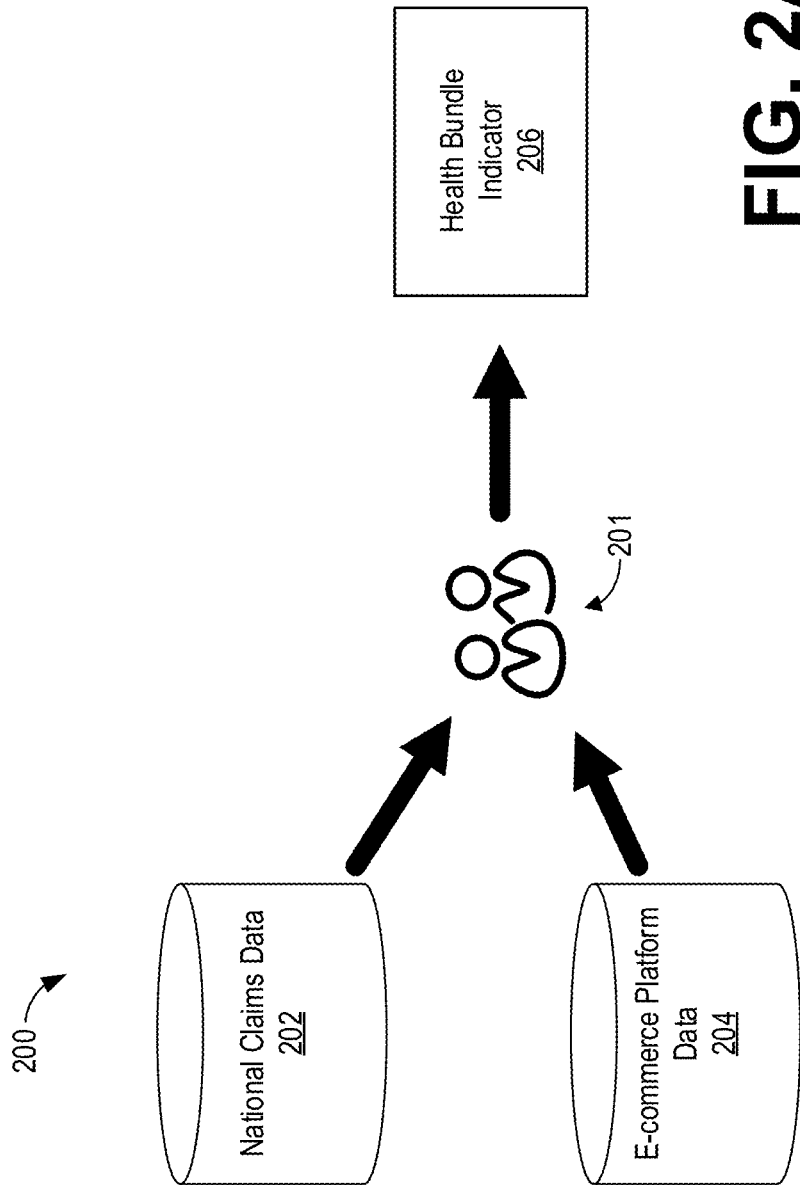

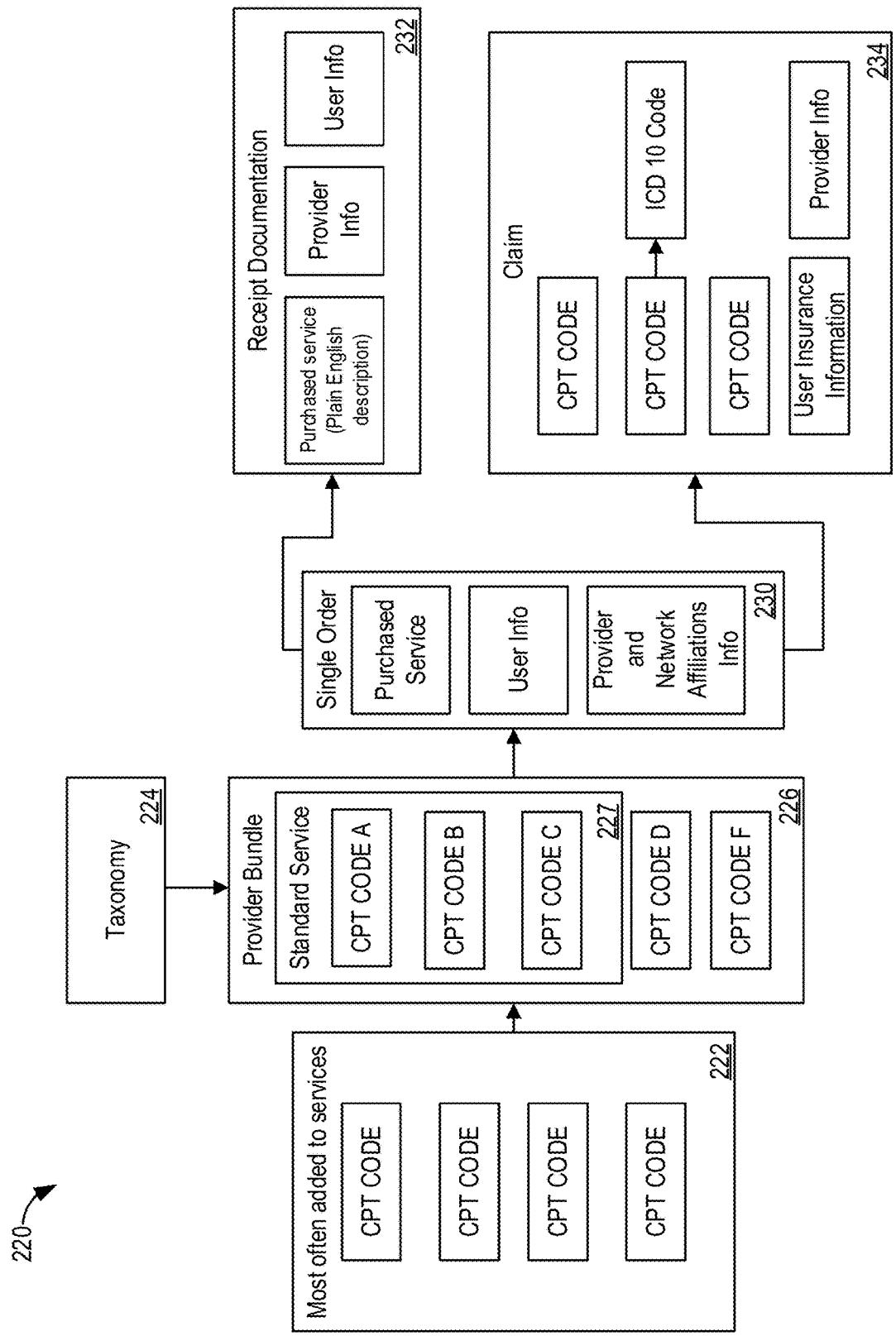

415

Health Care Marketplace — johnsmith

- 1. Practice ✓
- 2. Locations ✓
- 3. Providers ✓
- 4. Services ✓
- 5. Payment
- 6. Review and Submit 4.1 Procedures → 4.2 Services → 4.3 Locations → 4.4 Review    Add a Co-worker    Contact Us

Procedures

To save time, please start pricing by procedures. Then we'll take care of building your Wellness Exam catalog.

Leave blank any optional procedures not offered at your practice.

Wellness Exam procedures (required)

| Code | Description | Your fee | Comparison |
|---|---|---|---|
| 80061 | Lipid panel This panel must include the following: Cholesterol, serum total... | $ 20 | Regional: $28 |
| 82947 | Glucose; quantitative, blood (except reagent strip) | $ 10 | Regional: $8 |
| 87491 | Infectious agent detection by nucleic acid (DNA or RNA): Chlamydia trach... | $ 50 | Regional: $40 |
| 88174 | Cytopathology, cervical or vaginal (any reporting system), collected in... | $ 30 | Regional: $25 |
| 99385 | Initial comprehensive preventive medicine evaluation and management of... | $ 125 | Regional: $132 |
| 99386 | Initial comprehensive preventive medicine evaluation and management of... | $ 140 | Regional: $150 |
| 99395 | Initial comprehensive preventive medicine evaluation and management of... | $ 128 | Regional: $115 |
| 99396 | Period comprehensive preventive medicine reevaluation and management of... | $ 102 | Regional: $123 |

Wellness Exam procedures (optional)

| Code | Description | Your fee | Comparison |
|---|---|---|---|
| 99396 | Computer-aided detection (computer algorithm analysis of digital image data... | $ | Regional: $11 |

[ Save and Continue ]

| Health Care Marketplace | | | | |
|---|---|---|---|---|
| Order Management | | | | johnsmith |
| Service Offerings | Current service offerings | | | |
| Practice Profile | | | | |
| Dashboard | Primary Care: Wellness Exams (18 services) | | | |
| Marketing Tools | Service details | Pricing | | Comparison |
| Help | Man's Wellness Exam, age 18-34, new patient | Patient pays: $105 | Edit | Regional: $110 |
| | Man's Wellness Exam, age 18-34, established patient | Patient pays: $89 | Edit | Regional: $102 |
| | Man's Wellness Exam, age 18-34, new patient, history of high blood pressure | Patient pays: $152 | Edit | Regional: $160 |
| | Man's Wellness Exam, age 18-34, established patient, history of high blood pressure | Patient pays: $145 | Edit | Regional: $155 |
| | Man's Wellness Exam, age 35-39, new patient | Patient pays: $133 | Edit | Regional: $130 |
| | Man's Wellness Exam, age 35-39, established patient | Patient pays: $126 | Edit | Regional: $125 |
| | Man's Wellness Exam, age 35-39, new patient, history of high blood pressure | Patient pays: $169 | Edit | Regional: $173 |
| | Man's Wellness Exam, age 35-39, established patient, history of high blood pressure | Patient pays: $160 | Edit | Regional: $164 |
| | Man's Wellness Exam, age 40-49, new patient | Patient pays: $177 | Edit | Regional: $180 |
| | Man's Wellness Exam, age 40-49, established patient | Patient pays: $170 | Edit | Regional: $172 |
| | Man's Wellness Exam, age 40-49, new patient, history of high blood pressure | Patient pays: $195 | Edit | Regional: $204 |
| | Man's Wellness Exam, age 40-49, established patient, history of high blood pressure | Patient pays: $190 | Edit | Regional: $193 |
| | Man's Wellness Exam, age 50-64, new patient | Patient pays: $180 | Edit | Regional: $190 |
| | Man's Wellness Exam, age 50-64, established patient | Patient pays: $170 | Edit | Regional: $180 |
| | Man's Wellness Exam, age 50-64, new patient, history of high blood pressure | Patient pays: $211 | Edit | Regional: $214 |
| | Man's Wellness Exam, age 50-64, established patient, history of high blood pressure | Patient pays: $201 | Edit | Regional: $208 |
| | Woman's Wellness Exam, age 18-24, new patient | Patient pays: $141 | Edit | Regional: $130 |
| | Woman's Wellness Exam, age 18-24, established patient | Patient pays: $132 | Edit | Regional: $120 |

Locations [Edit]
Evergreen Urgent Care Clinic: John Smith, Jane Doe
Evergreen Wellness Clinic: John Smith, Jane Doe

FIG. 4C

Health Care Marketplace    Orders   Practice Info   Locations   Providers   Service Offerings     johnsmith    Log Out

Orders

| Upcoming (1) | Payment Pending (0) | Paid (0) | Cancelled (0) | | | |
|---|---|---|---|---|---|---|
| ◆ Order ID | ◆ Patient name | ◆ Service name | ◆ Provider | ◆ Location | ◆ Service fee | ◆ Order date |
| R36241479 | Sue Jones | Illness or Injury Visit – Minor Condition | John Smith | Evergreen Clinic | $100.00 | 03/25/2015   View Fulfill |

Displaying 1 Orders

Filters

ORDER ID
[ Contains ▼ ] [            ]

PATIENT LAST NAME
[ Contains ▼ ] [            ]

SERVICE NAME
[ Contains ▼ ] [            ]

PROVIDER
[ Contains ▼ ] [            ]

LOCATION
[ Contains ▼ ] [            ]

[ Filter ]   [ Clear Filters ]

Health Care Marketplace  Orders  Practice Info  Locations  Providers  Service Offerings     johnsmith   Log Out MERCHANT CONSOLE / ORDERS / MERCHANT ORDER #449
Fullfill order

Order Details

DATE OF SERVICE  March
25
2015

INVOICE NUMBER  2468

ACCOUNT NUMBER

Procedure codes

REQUIRED PROCEDURE CODE  99203 - OFFICE/OUTPATIENT VISIT, NEW

QUANTITY  1

DIAGNOSIS CODES  372.3 – UNSPECIFIED CONJUNCTIVITIS  X

OTHER DIAGNOSIS CODES

[ Get Paid ]  [ Cancel ]

| Health Care Marketplace | Orders  Practice Info  Locations  Providers  Service Offerings | johnsmith  Log Out |

MERCHANT CONSOLE / ORDERS /

Order

[ Edit ]

You have submitted this service order for payment. *NOTICE* There is no need to process a claim for this service.

ORDER: R241447746

Order Details

| | |
|---|---|
| ORDER ID | R241447746 |
| ORDER DATE | March 25, 2015 22:27 |
| STATUS | Pending payment |
| PROVIDER FEE | $100.00 |
| PROCESSING FEE | $3.20 |
| NET AMOUNT | $96.80 |
| SERVICE FEE | EMPTY |
| SERVICE DATE | March 25, 2015 |
| SUBMISSION DATE | March 25, 2015 |
| PAYMENT DATE | EMPTY |
| INVOICE NUMBER | 1234567 |
| ACCOUNT NUMBER | 2468 |
| PROCEDURE & DIAGNOSIS | 99203 – OFFICE OUTPATIENT VISIT, NEW | 372.3 – UNSPECIFIED CONJUNCITIVITIS |

Patient Details

| | |
|---|---|
| NAME | Sue Jones |
| PHONE NUMBER | 503-123-4567 |
| EMAIL ADDRESS | suejones@email.com |
| DATE OF BIRTH | January 1, 1990 |

Service Details

| | |
|---|---|
| NAME | Illness or Injury Visit -- Minor Condition |
| DESCRIPTION | This service is for a visit to a new health care provider for a minor condition which requires a visit to assess. It includes evaluation by the provider. Specific conditions included in this service are eye infection, ear infection, allergy symptoms, sinus infection, cough/bronchitis, hemorrhoids, vaginal infection, skin rash or infection, skin growth, or knee, ankle, elbow, shoulder, or foot pain. |
| SKU NUMBER | 26W-222J-222F |

Provider Details

| | |
|---|---|
| NAME | John Smith |
| LOCATION | 1 SW Address Street Portland OR 97201 |
| PHONE | 503-123-1234 |

How to cancel

To cancel this order, call 888-111-1111 Monday-Friday 7am to 5pm Pacific time to speak with a Provider Services representative.

Health Care Marketplace              suejones

Welcome.

Start shopping smart for health care services today. We'll show you prices in advance so you can make wallet-wise decisions.

| Search for a provider or health condition | Near | |
|---|---|---|
| illness or injury | Portland, OR | Search |

( Browse Our Services > )    ( Find Out About Telehealth > )

Need to speak to a doctor now?

With MDLIVE, you'll get instant access to board-certified physicians and licensed therapists by video conference or phone.      ( Connect with MDLIVE > )

Browse by category

Shop for services in    Portland, OR

| Allergy | Behavioral Health | Chiropractic, Acupuncture, and Massage | Dentistry |

Health Care Marketplace            suejones

←    Please verify your order details below

Details        Payment        Done!
① ─────────── 2 ─────────── 3

[ Cancel ] [ Proceed to Payment ]

Details

Who will be receiving care?

This service is for      ( Sue Jones ▼ )

Patient                  Sue Jones

Date of birth              01/01/1980

Do you want the Health Care Marketplace to file a claim for this service with your health plan?    ● Yes ○ No

*If you select "no," please note that you will be responsible for 100% of the provider price and your payment will not be applied to your deductible, unless you file a claim with your health plan on your own.*

Order summary

Illness or Injury Visit – Minor Condition (New Patient)
✓ HSA eligible

Provider
John Smith

Practice
Evergreen Clinic
100 SW Address Street
Portland, OR 97201
📍 (Map)
Phone: 503-123-4567
Email: johnsmith@evergreenclinic.com

Patient
Sue Jones

Provider price           $100.00
Plan pays              -$80.00
You pay:            $20.00

Cost Breakdown

| | Plan | Member |
|---|---|---|
| Co-insurance | $80.00 | $20.00 |
| Totals | $80.00 | $20.00 |

[ Cancel ] [ Proceed to Payment ]

Health Care Marketplace             suejones

← Please verify your order details below

Details — 1     Payment — 2     Done! — 3

[Cancel] [Proceed to Payment]

Details

Who will be receiving care?

This service is for: Sue Jones

Patient: Sue Jones
Date of birth: 01/01/1980

Do you want the Health Care Marketplace to file a claim for this service with your health plan? ● Yes ○ No

Order summary

Acupuncture – Initial Evaluation, 60 Minutes
ⓘ Conditionally HSA eligible

Provider
Another Provider

Practice
Downtown Clinic
100 SW Address Street
Portland, OR 97201
♀ (Map)
Phone: 503-123-4567
Email: johnsmith@evergreenclinic.com

Patient
Sue Jones

Provider price     $150.00
Plan pays     -$0.00
You pay:     $150.00

Cost Breakdown

| | Plan | Member |
|---|---|---|
| Co-insurance | $0.00 | $150.00 |
| Totals | $0.00 | $150.00 |

[Cancel] [Proceed to Payment]

Health Care Marketplace                          suejones

← Please verify your order details below

Details — 1      Payment — 2      Done! — 3

[Cancel] [Proceed to Payment]

Details

Who will be receiving care?

This service is for      [Sue Jones ▾]

Patient      Sue Jones
Date of birth      01/01/1980

Do you want the Health Care Marketplace to file a claim for this service with your health plan?     ● Yes  ○ No

*If you select "no," please note that you will be responsible for 100% of the provider price and your payment will not be applied to your deductible, unless you file a claim with your health plan on your own.*

Order summary

Annual Wellness Exam – Female 18-24 (Established Patient)
✓ HSA eligible

Provider
John Smith

Practice
Evergreen Clinic
100 SW Address Street
Portland, OR 97201
◉ (Map)
Phone: 503-123-4567
Email: johnsmith@evergreenclinic.com

Patient
Sue Jones

Provider price      $180.00
Plan pays      -$180.00
You pay:      $0.00

Cost Breakdown

| | Plan | Member |
|---|---|---|
| Co-insurance | $180.00 | $0.00 |
| Totals | $180.00 | $0.00 |

[Cancel] [Proceed to Payment]

Health Care Marketplace          suejones

←     Order complete! See below for next steps.

Details       Payment       Done!
(1) ——————— (2) ——————— (3)

[Print] [Continue Shopping]

Order confirmation for Sue Jones

Order ID R362451479       Ordered on: 03/25/2015

You've successfully purchased a Illness or Injury Visit– Minor Condition with John Smith Service Purchased:   Illness or Injury Visit – Minor Condition
                  HealthSKU 26W-222J-222F
Recipient:   Sue Jones
Amount Charged:   $20.00 to card ending with 1234

You saved 25%
*off the average regional price

Connect with your provider

Schedule your appointment with John Smith
Your provider has been notified about your order and should be ready to help.
1. Call your provider at 503-123-4567
2. Reference Order ID R362451479 to set up your appointment.

Practice location:      Office hours:
Evergreen Clinic         Mon-Fri 8:00 a.m. – 5:00 p.m.
100 SW Address Street   Sat-Sun Closed
Portland, OR 97201 (Map)

Need help scheduling your appointment? Call your Personal Health Assistant at 888-888-8888.

⚠ Special considerations
Free parking in the lot in the back of the building.

Order summary

Illness or Injury Visit – Minor Condition (New Patient)
✓ HSA eligible

Provider
John Smith

Practice
Evergreen Clinic
100 SW Address Street
Portland, OR 97201
(Map)
📞 Phone: 503-123-4567
Email: johnsmith@evergreenclinic.com

Patient
Sue Jones

Provider price          $100.00
Plan pays             -$80.00
You pay:            $20.00

Cost Breakdown
              Plan     Member
Co-insurance   $80.00   $20.00
Totals          $80.00   $20.00

[Continue Shopping]

[Rate Your Experience]

| Health Care Marketplace | | | | | | | suejones |
|---|---|---|---|---|---|---|---|
| ← Hi Sue! You can view your order history below... | | | | | | | |

Home > My Orders

My Orders

| Order ID | Order date | Service | Provider | Location | Status | Provider price | You paid |
|---|---|---|---|---|---|---|---|
| R362451479 | 03/25/2015 | Illness or Injury Visit – Minor Condition | John Smith | Evergreen Clinic | Rendered | $100.00 | $20.00 |

Health Care Marketplace
suejones

⬅ Order R362451479: eHealthReceipt™

Home > My Orders > Order R362451479: eHealthReceipt™

[Print]

Health Care Marketplace
100 SW Market St., Portland, OR 97201
855-864-2935
support@healthcaremarketplace.com eHealthReceipt
Order ID R362451479

Member information

Sue Jones
3000 SE Example Drive
Portland, OR 97215

Member ID
RWG1500000005

Health plan
HSA2.0/Preferred
CAMBIA HEALTH SOLUTIONS

Group number
6000008

Payment summary

| | |
|---|---|
| Provider price | $100.00 |
| Member responsibility (20%) | $20.00 |
| Plan responsibility (80%) | $80.00 |

Customer transactions

| Date | Source | Amount |
|---|---|---|
| 03/25/2015 | Charged to card ending in: 1234 | $20.00 |

Service summary

| Order ID | HealthSKU | Order date | Date of service |
|---|---|---|---|
| R362451479 | 26W-222J-222F | 03/25/2015 | 03/25/2015 |

Service
Illness or Injury Visit – Minor Condition

This service includes
assessment of a minor condition

Patient details

| Patient | Date of birth |
|---|---|
| Sue Jones | 01/01/1980 |

Provider details

| Provider | Practice Location |
|---|---|
| John Smith, MD | Evergreen Clinic<br>1 SW Address Blvd<br>Portland, OR 97201<br>503-123-4567 |

Claim information

| Quantity | Procedure | Diagnosis |
|---|---|---|
| 1 | 99203 OFFICE/OUTPATIENT VISIT, NEW | 372.3 UNSPECIFIED CONJUNCTIVITIS |

Health Care Marketplace  suejones

Compare providers

You've selected 3 providers to compare.  [Add More]                    [Back to Search Results]

| | John Smith, MD ⊗ | Bob Robert, MD ⊗ | Anne Doe, MD ⊗ |
|---|---|---|---|
| | [Add to Cart] | [Add to Cart] | [Add to Cart] |
| Service | Injury or illness visit (details) | Injury or illness visit (details) | Injury or illness visit (details) |
| Price | $89.00 | $89.00 | $108.00 |
| Duration | 20 minutes | 20 minutes | 20 minutes |
| Patient reviews | ★★★★☆ (28 reviews) | ★★★☆☆ (17 reviews) | ★★★★★ (28 reviews) |
| Specialty | General practitioner | Natural health | General practitioner |
| Language | English | English, Spanish | English, Spanish |
| Distance | 1.8 miles | 2.2 miles | 1.9 miles |
| Practice | Evergreen Clinic | Another Clinic | Portland Health |
| Address | 100 SW Address St. Portland, OR 97202 (map) | 123 NE Broadway Ave. Portland, OR 97216 | 1234 NW Burnside St. Portland, OR 97209 |
| Office phone | 503-123-4567 | 503-111-2222 | 503-999-9999 |
| Hours | Mon-Fri: 9 a.m. – 5 p.m. Sat-Sun: Closed | Mon-Fri: 9 a.m. – 5 p.m. Sat-Sun: Closed | Mon-Fri: 9 a.m. – 5 p.m. Sat: 9 a.m. – 12 p.m. Sun: Closed |
| Quality rating | A+ | A+ | N/A |

FIG. 6L

SYSTEMS AND METHODS FOR A HEALTH CARE E-COMMERCE MARKETPLACE

CROSS REFERENCE TO RELATED APPLICATIONS

The present application is a divisional of U.S. patent application Ser. No. 14/845,170, entitled "SYSTEMS AND METHODS FOR A HEALTH CARE E-COMMERCE MARKETPLACE," filed Sep. 3, 2015, which claims priority to U.S. Provisional Patent Application No. 62/048,157, entitled "SYSTEMS AND METHODS FOR AN ONLINE HEALTH CARE MARKETPLACE," filed on Sep. 9, 2014. The entire contents of each of the above-mentioned applications are hereby incorporated by reference for all purposes.

BACKGROUND/SUMMARY

In the modern world, consumers are accustomed to a wide array of options when shopping for goods and services. Furthermore, online shopping enables consumers to make an informed purchasing decision by comparing products by price and quality, for example. However, in today's health care marketplace, consumers are unable to shop for health care services, which may include medical treatments, dental services, mental health services, prescriptions, alternative health services, and any other medical services or goods, the way they shop for virtually every other good and service.

Indeed, health care consumers are often uninformed regarding the expenses they are incurring when purchasing health care services. For example, health care consumers are currently limited to visiting a health care provider in order to receive health care services without knowing how much the services will cost until the health care consumer receives an Explanation of Benefits (EOB) statement from his or her health insurance company and a bill from the health care provider. Such EOB statements typically outline the services rendered by using cryptic common procedure terminology (CPT) codes.

The price of health care services is further obscured by the variability of health care plan benefits. For health care consumers, identifying what health care services may be covered by a health care plan is exceedingly difficult, let alone understanding the extent of coverage. Even when a health care consumer eventually receives an EOB statement, he or she may be surprised to find that his or her health insurance does not cover a health care service that the health care consumer already received and expected to be covered.

Aside from the obfuscation of health care insurance benefits, health care services and associated prices are highly variable from provider to provider. Such variability results from complex contractual agreements between providers and insurance companies. As a result, health care consumers may expect to pay a particular price for a health care service based on previous experience, only to discover that a different provider charges a different price for the same health care service. Given the closed nature of the current health care marketplace, even health care providers themselves may not be aware of how much they differ cost-wise from other providers.

The deficiencies of the health care marketplace not only negatively affects health care consumers, but health care providers as well. For example, health care providers provide health care services prior to receiving payment. Furthermore, health care providers may be delayed in receiving payment for their services from a health care consumer for an indeterminate amount of time, possibly resulting in a prolonged debt collection situation that everyone involved would prefer to avoid.

Thus, health care consumers need a standardized way to shop for and compare health care services. The inventors have recognized the above issues and have devised several approaches to address them. In particular, systems and methods for a health care e-commerce marketplace are provided. In one embodiment, a method comprises, responsive to a query from a user, retrieving from a database a list of responses comprising one or more health care providers offering one or more health care services at a provider-supplied price; filtering the list of responses based on a geographic location included in the query; providing, for display, the filtered list of responses; receiving a payment from the user for a response selected from the filtered list of responses; automatically sending a notification of the payment to a provider associated with the selected response; and responsive to receiving an order fulfillment notification from the provider, automatically providing the payment to the provider. In this way, health care consumers may make informed purchasing decisions when shopping for health care services and health care providers may receive prompt payment for services delivered.

In another embodiment, a computer-readable storage medium includes an executable program stored thereon, the program configured to cause a computer processor to: retrieve health care claims data from one or more databases; process the health care claims data to identify a combination of current procedural terminology (CPT) codes provided to a plurality of patients in a single health care interaction; assemble the combination of CPT codes into a bundle of health care services; generate a product code for a bundle of health care services; receive a price for the product code from a health care provider; generate a health care service bundle indicator for the health care provider based on the product code; and assign the price to the health care service bundle indicator. In this way, health care services offered by health care providers may be normalized and health care consumers may shop for and purchase health care service bundle indicators in a health care e-commerce marketplace.

In another embodiment, an apparatus facilitating a health care marketplace comprises a processor and memory storing processor-executable instructions that cause the processor to: receive, from a user, a payment for a bundle of health care services provided by a health care provider prior to the user visiting the health care provider; automatically generate receipt documentation responsive to receiving an order fulfillment notification from a health care provider indicating that the user received the bundle of health care services from the health care provider, wherein the receipt documentation includes one or more current procedural terminology (CPT) codes associated with the bundle of health care services; send, to the user, the receipt documentation formatted for display to the user and including a non-technical description of the one or more CPT codes; and send, to an insurance administrator for a health insurance plan of the user, the receipt documentation formatted as a health care claim. In this way, health care consumers can easily track their health care spending and health care providers no longer need to deal with writing and submitting health care claims to insurance administrators.

The above summary is provided to introduce a selection of concepts in a simplified form that are further described below in the Detailed Description. This summary is not intended to identify key features or essential features of the subject matter, nor is it intended to be used to limit the scope of the subject matter. Furthermore, the subject matter is not limited to implementations that solve any or all of the disadvantages noted above or in any part of this disclosure.

BRIEF DESCRIPTION OF THE FIGURES

FIGS. 2A-2B illustrate example methods for bundling health care services into a health care service bundle indicator.

FIGS. 4A-4F illustrate example e-commerce health care platform interfaces for a health care provider.

FIGS. 6A-6L illustrate example e-commerce health care platform interfaces for a health care consumer.

DETAILED DESCRIPTION

Figure 5:
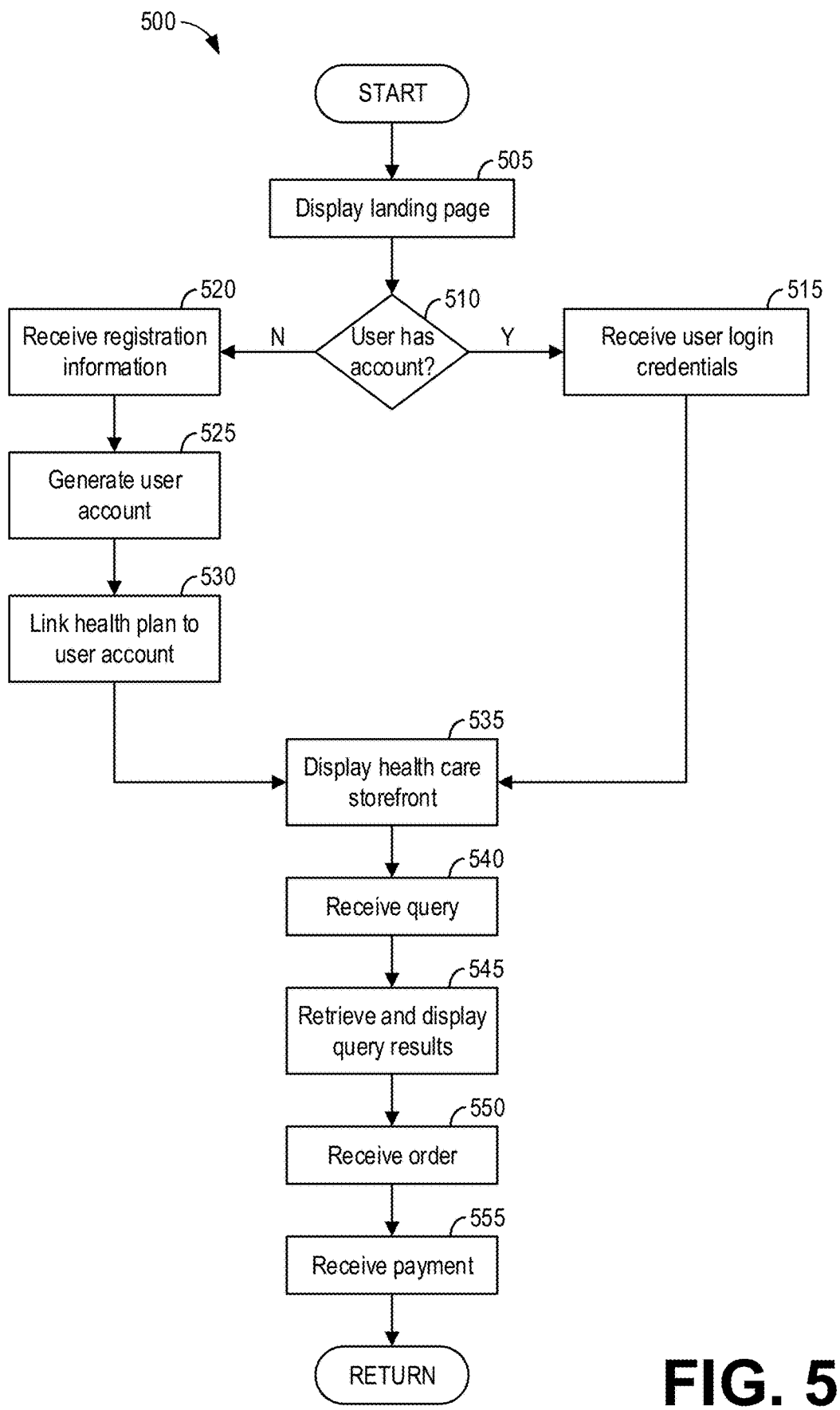
FIG. 5 shows a high-level flow chart illustrating an example method for a health care consumer using an e-commerce health care platform.
Figure 7:
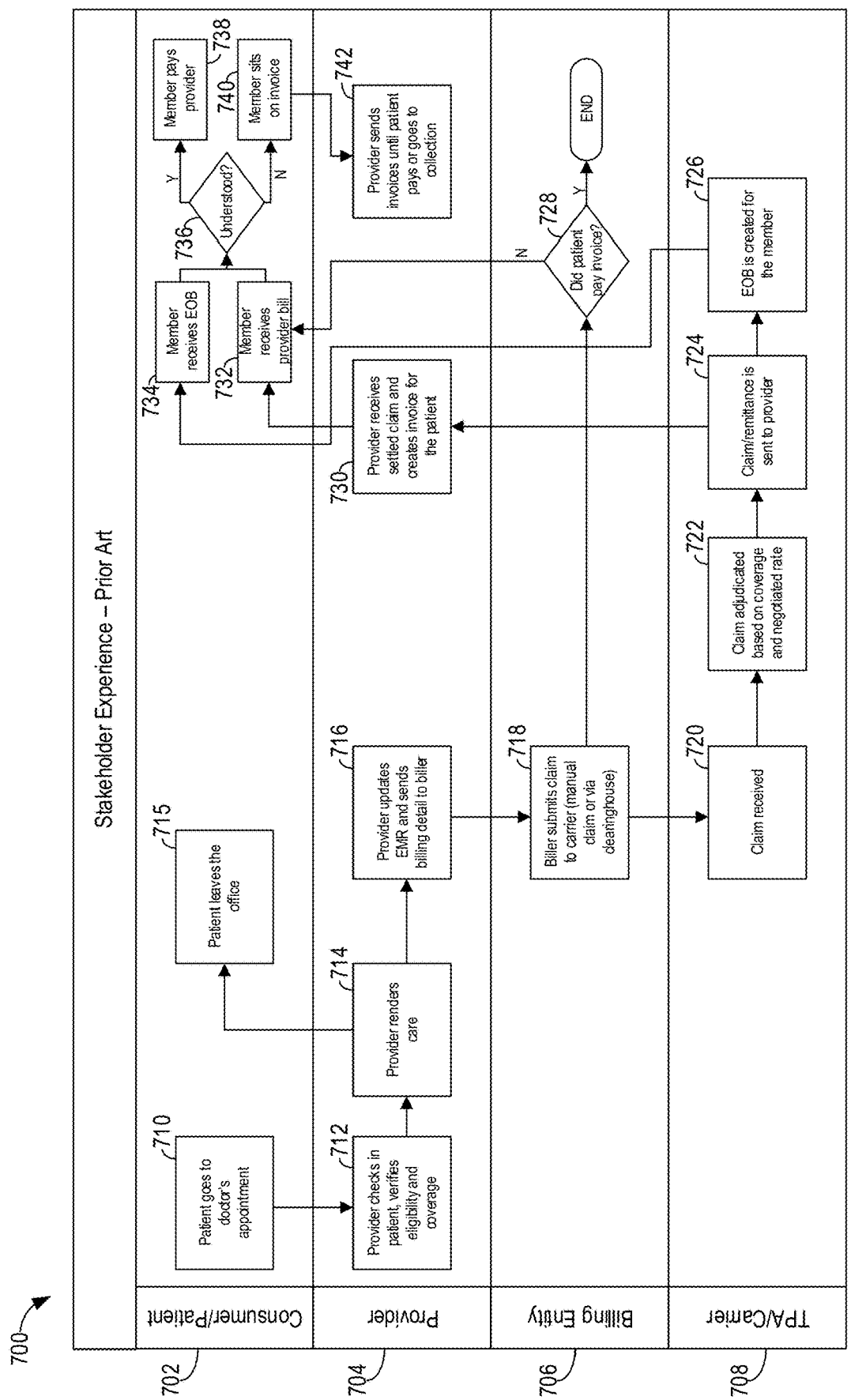
FIG. 7 shows a high-level flow chart illustrating an example method for providing and billing for health care services according to prior art.
Figure 8:
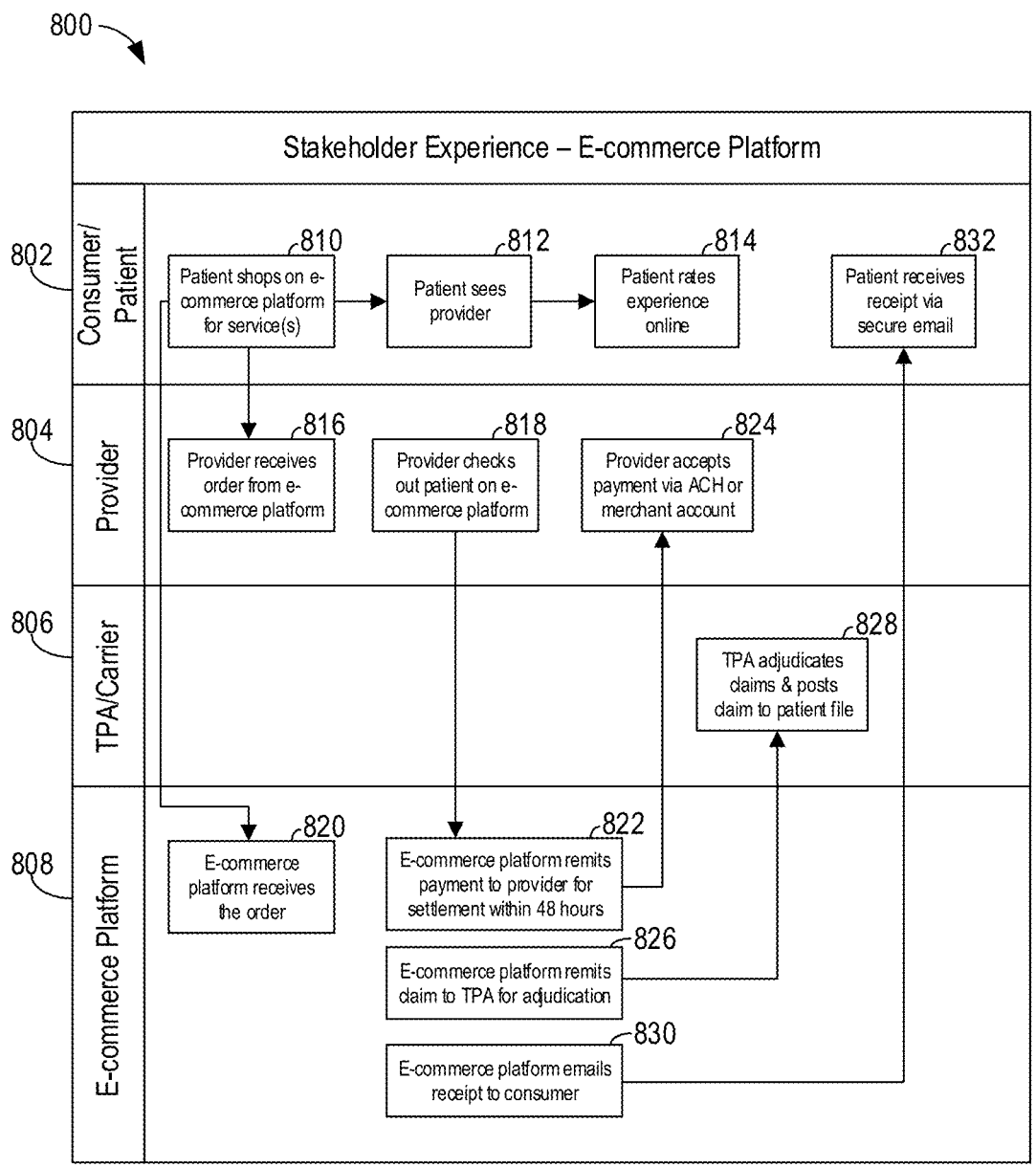
FIG. 8 shows a high-level flow chart illustrating an example method for providing and billing for health care services with an e-commerce health care platform.
Figure 9:
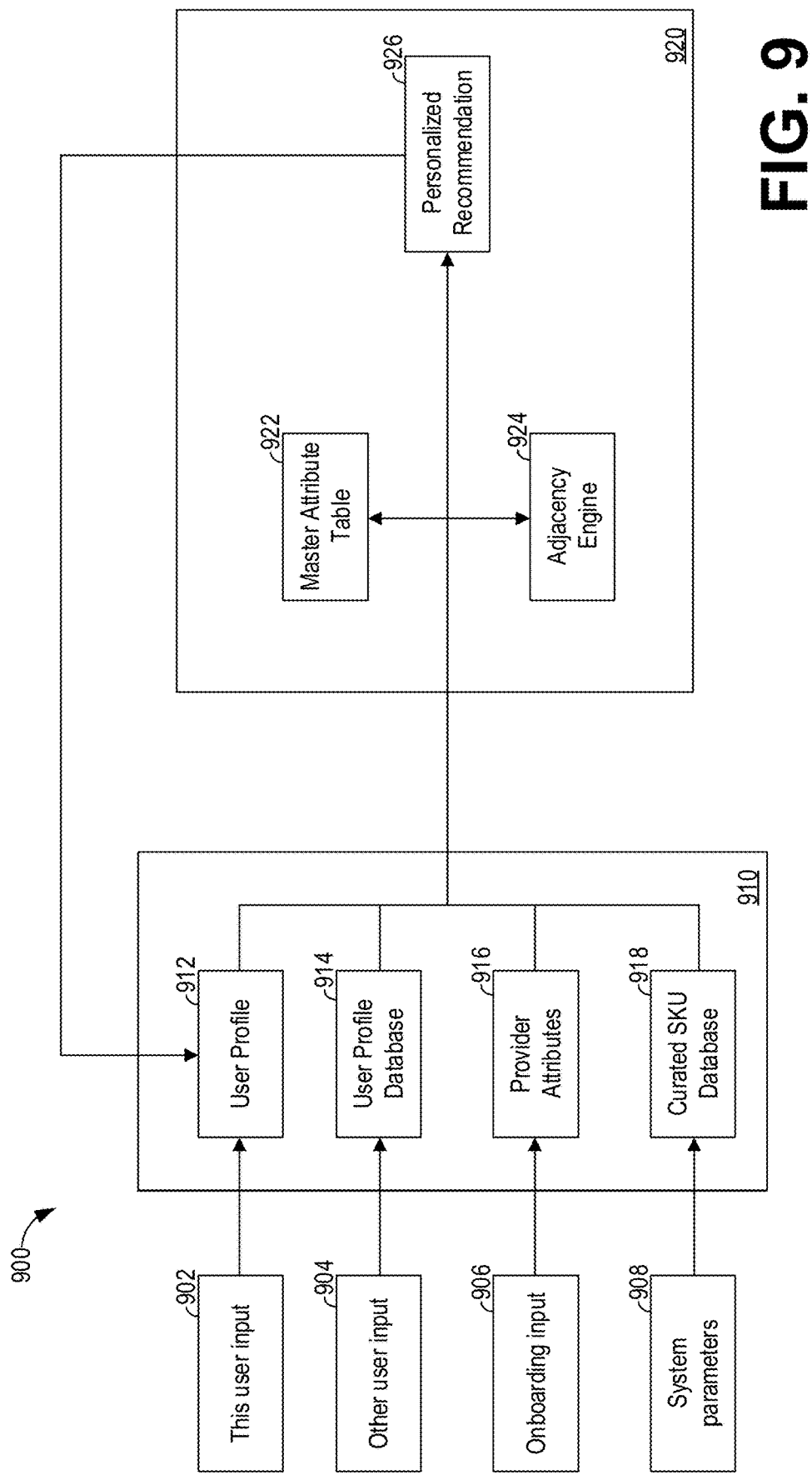
FIG. 9 illustrates an example method for personalizing an e-commerce health care platform for a health care consumer.

The present description relates to systems and methods for an e-commerce health care marketplace. In particular, systems and methods are provided for selling standardized bundles of health care services. Consumers need a way to shop for and compare health care services in a standardized way. Today, provider services and pricing are highly variable, and consumers cannot easily compare services because of variations in CPT codes when shopping for and selecting these services. The systems shown in FIGS. 1A-1D provide for the formation of a standardized bundle of care that can be stocked and sold in an e-commerce marketplace. As shown in FIGS. 2A-2B, the goal of the standardized bundle of care, referred to herein interchangeably as a health care service bundle indicator or a HEALTHSKU™ indicator, is to curate the health care service shopping experience in a way that is meaningful and easily understood by the consumer. This health care service bundle indicator comprises a sequence of alphanumeric characters which identify a defined set of CPT codes, a provider and any network affiliations, and a geographic location of the provider. A health care provider may enroll in and use the e-commerce marketplace platform via several methods, such as those shown in FIGS. 3A-3C. As shown by FIGS. 4A-4F, the health care service bundle indicator will be stocked by providers on an e-commerce platform, and providers can set up an account on the e-commerce platform such that payment for the bundled health care services, which have provider-adjustable prices, is facilitated by the e-commerce platform. As shown by FIGS. 5-6L, health care service bundle indicators may be purchased by consumers through the e-commerce platform before visiting a health care provider. The e-commerce platform may take health care plan coverage into consideration so that consumers do not need to be reimbursed later. After a health care consumer purchases a health care service bundle indicator, a provider fulfills the order. In addition to simplifying a health care consumer's experience of purchasing health care services, the system described herein further simplifies the billing system overall, as depicted in FIGS. 7-8. As consumers and providers utilize the e-commerce platform, over time the e-commerce platform offers personalized health care service bundle indicator recommendations for users, as depicted in FIG. 9.

Figure 1A:
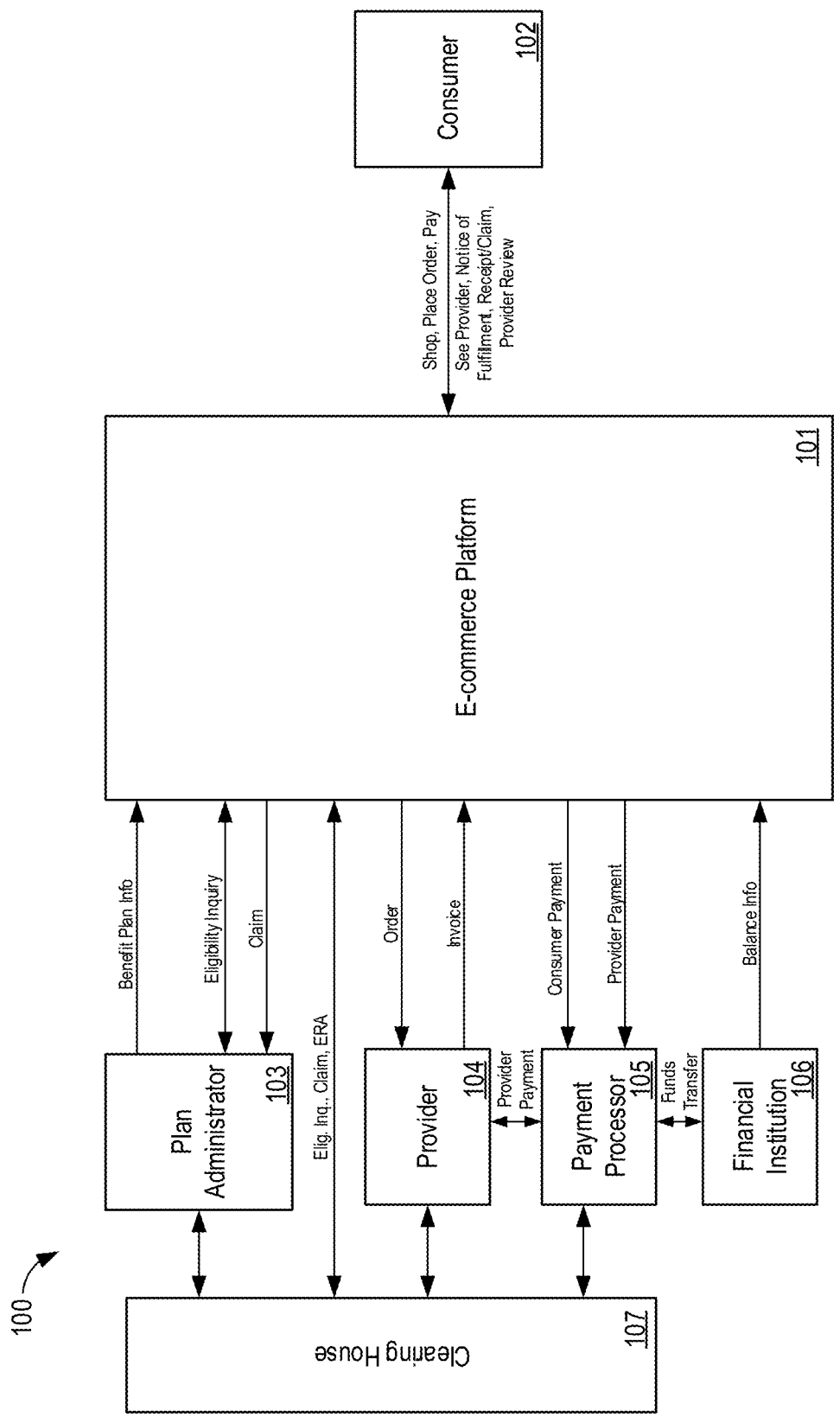
FIGS. 1A-1D show high-level illustrations of an example e-commerce health care platform.

FIG. 1A shows a high-level diagram illustrating an example health care system 100 in accordance with the current disclosure. In particular, health care system 100 illustrates how an e-commerce platform 101 may facilitate the selling and purchasing of health care services between a health care consumer 102 and a health care provider 104, with additional interaction between the e-commerce platform 101 and a health care plan administrator 103, a payment processor 105, a financial institution 106, and a clearinghouse 107.

Figure 1B:
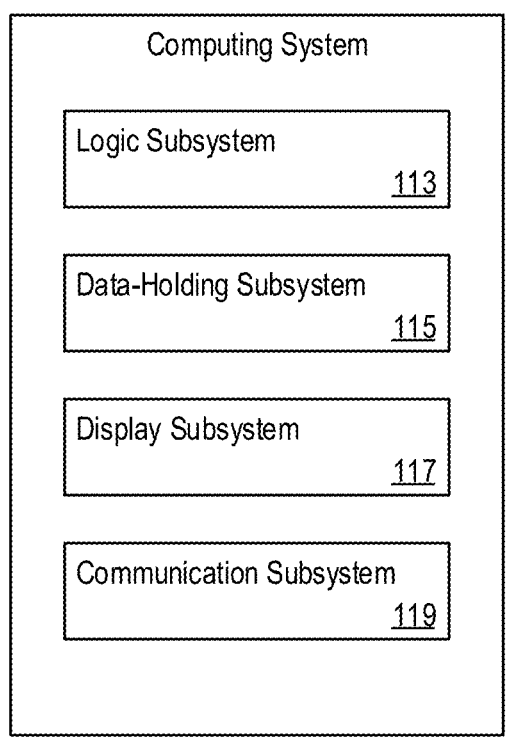

As described further herein with regard to FIG. 1B, each component of health care system 100 depicted in FIG. 1A may represent one or more computing devices capable of transmitting information, and the interactions between components may represent the flow of information between each computing device. As such, health care system 100 may be considered a computing environment in accordance with the current disclosure. Each computing device, such as the e-commerce platform 101, is shown in simplified form. However, each computing device in health care system 100 may take the form of one or more personal computers, server computers, tablet computers, home entertainment computers, network computing devices, mobile computing devices, mobile communication devices, and/or other computing devices. Each computing device in health care system 100 may include one or more displays for displaying an interface. For example, a provider device may include a display for displaying interfaces such as the interfaces described further herein and with regard to FIGS. 4A-4F, while a health care consumer computing device may include a display for displaying interfaces such as the interfaces described further herein and with regard to FIGS. 6A-6L.

In particular, health care system 100 is facilitated by the e-commerce platform 101. For example, a consumer 102 may shop, place an order, pay for the order, see a provider, receive a notice of fulfillment, and submit a provider review through the e-commerce platform 101 without the need to directly interact with any other entity in the health care system 100. The e-commerce platform 101 may place an order with a provider 104 and receive an invoice therefrom.

The e-commerce platform 101 may receive balance information for a health savings account (HSA) from a financial institution 106. If funds from an HSA are applied to the purchase of a health care service bundle indicator, funds are transferred between the financial institution 106 and the payment processor 105. E-commerce platform 101 provides the payment processor 105 a consumer payment and a provider payment. In some examples, the payment processor 105 is a part of the e-commerce platform 101.

Medical claims clearinghouse 107 interfaces with the plan administrator 103, the provider 104, the payment processor 105, and the e-commerce platform 101. In some examples, the clearinghouse 107 and the e-commerce platform 101 may directly communicate regarding eligibility inquiries, claims, and electronic remittance advice.

Health bundle indicators are formed using a national data set of the most common CPT codes associated with planned and predictable, routine health care services. These CPT codes are grouped to form common bundles of care. Health bundle indicators are loaded into the e-commerce platform along with the average prices of these bundles of care by region. Providers 104 can select which health care service bundle indicators to offer on the platform and offer the default average price or set their own price. Providers will compete in this open e-commerce marketplace on price and quality, driving down the costs associated with these services. Consumers 102 will be able to shop by price and quality for these standardized services, where a particular health care service bundle indicator is the same offering regardless of provider. Consumers 102 can purchase the health care service bundle indicator on the e-commerce platform 101. Health care service bundle indicators are described further herein and with regard to FIGS. 2A-2B.

Providers would like to simplify their administrative processes, particularly the bill review cycle, and eliminate claims complexity. Providers would like to improve their cash flow and reduce patient receivables. Consumers would also like to eliminate the uncertainty or surprise of unexpected bills associated with services received.

Thus, systems and methods are provided for making bundles of care look like a health care service bundle indicator to consumers, procedure and diagnosis codes to providers, and auto-adjudicated claims to a TPA. The e-commerce platform eliminates the normal processing overhead associated with claims, instead issuing receipt documentation, referred to herein also as an EHEALTHRECEIPT™, for services rendered. This receipt documentation will be issued to consumers while also being auto-adjudicated by their insurer to apply against their health plan deductible. Consumers will no longer have to receive or reconcile bills from their provider and their health plan's Explanation of Benefits (EOB) statement.

The e-commerce platform 101 enables providers to set their own fees and attract insured patients. Money from consumers will be placed into escrow and transfers between an account at financial institution 106 and the payment processor 105 will be configured before services are rendered, ensuring prompt payment to providers for patient services with no financial risk, reducing their patient receivables and improving their cash flow.

When health care consumers 102 register on the e-commerce platform 101, it confirms their eligibility in real time. The e-commerce platform 101 submits an eligibility inquiry to the plan administrator 103, and the plan administrator 103 returns a response. Consumers pay at the point of purchase on the e-commerce platform 101, and funds are released from the payment processor 105 to a provider 104 once the provider 104 confirms that purchased services were rendered by submitting an invoice, or claim. This eliminates the need for providers 104 to file a claim to a plan administrator 103 and for any surprise bills to consumers 102. Once this verification takes place, the information is released by the e-commerce platform 101 to the plan administrator 103 in the form of a claim, or receipt documentation, with a high probability of auto-adjudication. The plan administrator 103 processes the claim and applies it against the consumer's deductible. Example methods for billing are described further herein and with regard to FIGS. 7-8.

Health care professionals provide care to consumers and bill for these services using Current Procedural Terminology (CPT) codes that describe the medical procedures and physicians services provided to the patient. The consumer is not aware of the cost of these services before visiting the physician and health care services are highly variable across providers, making shopping for services difficult. Thus, systems and methods are provided for shopping, purchasing, and fulfilling normalized health care services from health care professionals online. E-commerce platform 101 provides a simple and easy way to understand, access, compare, and purchase care before appointment. The present invention relates to an improved process where planned and predictable health care services are purchased and consumed at known prices. Hence, an e-commerce health care marketplace is provided where consumers shop and pay for planned and predictable health care services at known prices. The e-commerce platform 101 helps consumers spend their limited health care dollars wisely by delivering transparent quality and cost information.

The e-commerce platform 101 enables health care consumers to: shop for health care services; shop and compare providers based on price, quality, and patient reviews; see where they stand with deductibles and calculate out-of-pocket costs; and order a service and pay for it using a personal credit/debit card or an HSA, FSA, or HRA account. Payments are processed and applied to deductibles after services are rendered, eliminating surprise bills later. Consumers can also access a nurse line or telehealth providers to seek help in finding the right health care service. Example methods and interfaces for health care consumers are described further herein and with regard to FIGS. 5-6L.

Consumers might need guidance when purchasing health care services. As first time shoppers in health care, they will want to know which types of services are often purchased together and what kind of modifications to their purchase might take place at the provider's office. They will need clarity that they are purchasing the right services at the right time. Thus, systems and methods are provided for the formation of a personalization engine. Similar to the online shopping sites consumers already use for products, consumers will receive recommendations for services based on their past purchases and the purchases of other consumers. Consumers will be able to see which health care service bundle indicators are commonly purchased together, and what modifications and add-ons might take place at the point of service. An example personalization engine is described further herein and with regard to FIG. 9.

FIG. 1B schematically shows a non-limiting computing system 110 that may perform one or more of the methods and processes described herein. As described hereinabove, any of the components shown in FIG. 1A may comprise computing system 110. It is to be understood that virtually any computer architecture may be used for a computing device without departing from the scope of this disclosure. In different embodiments, computing system 110 may take the form of a mainframe computer, server computer, desktop computer, laptop computer, tablet computer, home entertainment computer, network computing device, mobile computing device, mobile communication device, gaming device, etc.

Computing system 110 includes a logic subsystem 113 and a data-holding subsystem 115. Computing system 110 may optionally include a display subsystem 117, communication subsystem 119, and/or other components not shown in FIG. 1B. For example, computing system 110 may also optionally include user input devices such as keyboards, mice, game controllers, cameras, microphones, and/or touch screens.

Logic subsystem 113 may include one or more physical devices configured to execute one or more instructions. For example, logic subsystem 113 may be configured to execute one or more instructions that are part of one or more applications, services, programs, routines, libraries, objects, components, data structures, or other logical constructs.

Such instructions may be implemented to perform a task, implement a data type, transform the state of one or more devices, or otherwise arrive at a desired result.

Logic subsystem 113 may include one or more processors that are configured to execute software instructions. Additionally or alternatively, the logic subsystem 113 may include one or more hardware or firmware logic machines configured to execute hardware or firmware instructions. Processors of the logic subsystem 113 may be single core or multi-core, and the programs executed thereon may be configured for parallel or distributed processing. The logic subsystem 113 may optionally include individual components that are distributed throughout two or more devices, which may be remotely located and/or configured for coordinated processing. One or more aspects of the logic subsystem 113 may be virtualized and executed by remotely accessible networked computing devices configured in a cloud computing configuration.

Data-holding subsystem 115 may include one or more physical, non-transitory devices configured to hold data and/or instructions executable by the logic subsystem 113 to implement the herein described methods and processes. When such methods and processes are implemented, the state of data-holding subsystem may be transformed (for example, to hold different data).

Data-holding subsystem 115 may include removable media and/or built-in devices. Data-holding subsystem 115 may include optical memory (for example, CD, DVD, HD-DVD, Blu-Ray Disc, etc.), and/or magnetic memory devices (for example, hard disk drive, floppy disk drive, tape drive, MRAM, etc.), and the like. Data-holding subsystem 115 may include devices with one or more of the following characteristics: volatile, nonvolatile, dynamic, static, read/write, read-only, random access, sequential access, location addressable, file addressable, and content addressable. In some embodiments, logic subsystem 113 and data-holding subsystem 115 may be integrated into one or more common devices, such as an application specific integrated circuit or a system on a chip.

It is to be appreciated that data-holding subsystem 115 includes one or more physical, non-transitory devices. In contrast, in some embodiments aspects of the instructions described herein may be propagated in a transitory fashion by a pure signal (for example, an electromagnetic signal, an optical signal, etc.) that is not held by a physical device for at least a finite duration. Furthermore, data and/or other forms of information pertaining to the present disclosure may be propagated by a pure signal.

When included, display subsystem 117 may be used to present a visual representation of data held by data-holding subsystem 115. As the herein described methods and processes change the data held by the data-holding subsystem 115, and thus transform the state of the data-holding subsystem 115, the state of display subsystem 117 may likewise be transformed to visually represent changes in the underlying data. Display subsystem 117 may include one or more display devices utilizing virtually any type of technology. Such display devices may be combined with logic subsystem 113 and/or data-holding subsystem 115 in a shared enclosure, or such display devices may be peripheral display devices.

When included, communication subsystem 119 may be configured to communicatively couple computing system 110 with one or more other computing devices. Communication subsystem 119 may include wired and/or wireless communication devices compatible with one or more different communication protocols. As non-limiting examples, communication subsystem 119 may be configured for communication via a wireless telephone network, a wireless local area network, a wired local area network, a wireless wide area network, a wired wide area network, etc. In some embodiments, communication subsystem 119 may allow computing system 110 to send and/or receive messages to and/or from other devices via a network such as the public Internet.

Figure 1C:
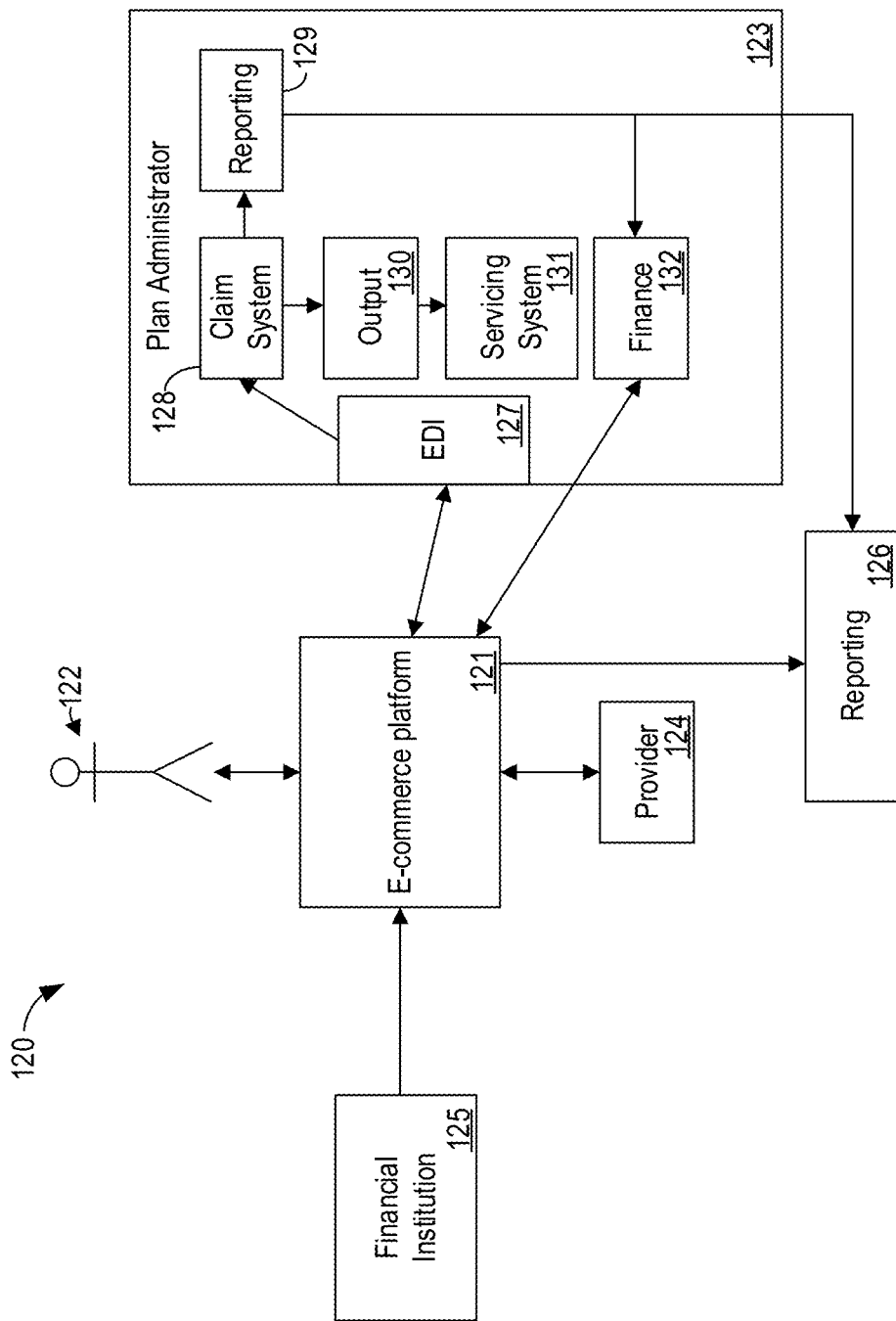

FIG. 1C shows a high-level diagram illustrating an example health care system 120 in accordance with the current disclosure. In particular, diagram 120 provides a zoomed-in, detailed view of a portion of health care system 100 with a focus on information flow between the e-commerce platform 121 and the consumer 122, a financial institution 125, a provider 124, a plan administrator 123, and a reporting system/clearinghouse 126.

Consumer 122 may interact with the e-commerce platform 121 to provide and retrieve account information, schedules, and payments. Similarly, the provider 124 may interact with the e-commerce platform 121 to provide and retrieve schedules and payments. To further facilitate payment to the provider 122, the e-commerce platform 121 may retrieve an account balance, such as an HSA balance, from the financial institution 125.

E-commerce platform 121 additionally interacts with a plan administrator 123, where the plan administrator 123 administers claims processing for a health care plan of the consumer 122. To that end, plan administrator 123 includes an electronic data interchange (EDI) system 127, claim system 128, reporting system 129, output system 130, servicing system 131, and finance system 132. The e-commerce platform 121 interacts with plan administrator 123 via EDI system 127. Specifically, the e-commerce platform 121 exchanges eligibility information and claim information with the EDI system 127. Claim system 128 processes the claim information received via the EDI system 127, output system 130 prepares output based on the processed claim information. Servicing system 131 and reporting system 129 handle administration of the processed claim information. For example, reporting system 129 communicates with finance system 132, which may further communicate with e-commerce platform 121, to facilitate payments to the provider 124 based on the claim information. Reporting system 129 may further communicate with clearinghouse 126, which may also separately receive eligibility information and claim information from e-commerce platform 121, such that the clearinghouse 126 may process and standardize reports.

Figure 1D:
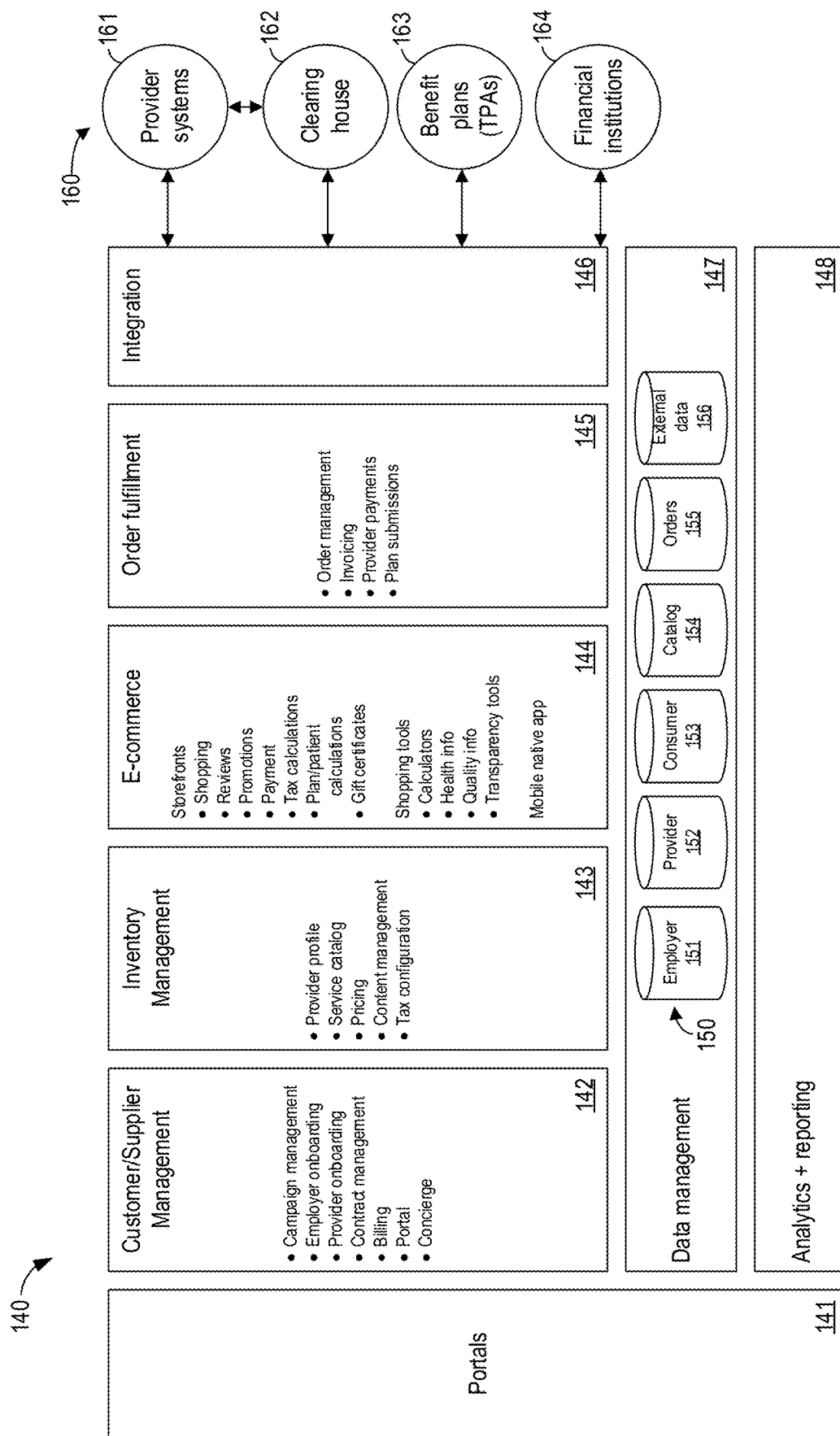

FIG. 1D shows a high-level diagram illustrating an example architecture 140 for an e-commerce platform in accordance with the current disclosure. Architecture 140 includes a plurality of modules configured to provide the functionality of an e-commerce platform, such as e-commerce platform 101 described herein above with regard to FIG. 1A. The plurality of modules may include, but are not limited to, a portals module 141, a customer/supplier management module 142, an inventory management module 143, an e-commerce module 144, an order fulfillment module 145, an integration module 146, a data management module 147, and an analytics and reporting module 148.

Portals module 141 provides interfaces that enable users of the e-commerce platform to interact with other modules of the plurality of modules 150. Example interfaces that may be provided by portals module 141 are described further herein.

Customer/supplier management module 142 provides campaign management, employer onboarding, provider onboarding, contract management, billing, portal, and a concierge. Consumer onboarding is described further herein with regard to FIGS. 5-6L, and provider onboarding is described further herein with regard to FIGS. 3A-4F.

Inventory management module 143 provides a provider profile, service catalog, pricing, content management, and tax configuration.

E-commerce module 144 provides multiple storefronts for health care services, each providing interfaces for shopping, reviews, promotion, payment, tax calculations, plan/patient calculations, and gift certificates. The e-commerce module further includes shopping tools, such as calculators, health information, quality information, and transparency tools. The e-commerce module 144 also provides a mobile native application that enables a health care consumer to interact with the e-commerce platform through a mobile device.

Order fulfillment module 145 provides order management, invoicing, provider payments, and plan submissions.

Integration module 146 provides interfaces for communicating with systems external to the e-commerce platform, including but not limited to provider systems 161, clearinghouses 162, benefit plans (e.g., via third-party administrators or TPAs) 163, and financial institutions 164.

Data management module 147 includes a plurality of databases 150, including one or more databases for each of an employer 151, provider 152, consumer 153, health plan, TPA, catalog 154, orders 155, and external data 156. Architecture 140 further includes an analytics and reporting module 148 for analyzing internal and external data as well as generating reports for internal and external review.

The systems described herein above with regard to FIGS. 1A-1D enable a simplified method for facilitating the selling and purchasing of health care services with an e-commerce platform. Specifically, such a method relates to the purchasing of prepackaged health care services prior to receiving the health care services from a health care provider. In this way, prices for health care services may be lowered due to competition, providers may receive payment more quickly for services rendered, and health care consumers may shop for health care without being surprised by a health care bill weeks after receiving a health care service.

As an illustrative example, providers may list services and prices for the services using the e-commerce platform. The marketplace provided by the e-commerce platform leads to competitive pricing for health care services, as health care providers may view the prices for health care services offered by each other and compete for health care consumers. Methods and interfaces for health care providers provided by the e-commerce platform are described further herein and with regard to FIGS. 3A-4F.

Health care consumers may shop for health care services by comparing and choosing needed care. The e-commerce platform integrates with health care benefits to display the deductible impact to the health care consumer. A health care consumer may lock in the price of a chosen health care service with a health savings account (HSA), a flexible spending account (FSA), and/or a debit or credit card. Methods and interfaces for consumers pre-purchasing health care services are described further herein and with regard to FIGS. 5-6L.

The payment for health care services is securely held until care is received by the health care consumer. After the health care consumer and provider connect and care is delivered, receipt documentation is sent to a claims administrator in a format compliant with official standards, and payment is sent to the health care provider. The receipt documentation is also sent to the consumer in a user-friendly format. Methods and interfaces for a billing system are described further herein and with regard to FIGS. 7-8.

Consumers need a way to shop for and compare health care services in a standardized way. Today, provider services and pricing are highly variable, and consumers cannot easily compare services because of variations in CPT codes when shopping for and selecting these services. Thus, systems and methods for the formation of a standardized bundle of care that can be stocked and sold in an e-commerce marketplace are described further herein with regard to FIGS. 2A-2B. The goal of the standardized bundle of care, or health care service bundle indicator, is to curate the health care service shopping experience in a way that is meaningful and easily understood by the consumer. This health care service bundle indicator comprises a defined set of CPT codes, modifiable by provider, with associated average regional pricing. The health care service bundle indicator will be stocked by providers on an e-commerce platform and purchased by consumers.

Health bundle indicators are generated using a national data set of the most common CPT codes associated with planned and predictable, routine health care services. These CPT codes are grouped to form common bundles of care. Health bundle indicators are loaded into the e-commerce platform along with the average prices of these bundles of care by region. Providers can select which health care service bundle indicators to offer on the platform and offer the default average price or set their own price. Providers will compete in this e-commerce marketplace on price and quality, driving down the costs associated with these services. Consumers will be able to shop by price and quality for these standardized services, where a particular health care service bundle indicator is the same offering regardless of provider. Consumers can purchase the health care service bundle indicator on the e-commerce platform.

FIG. 2A shows a high-level diagram illustrating an example method 200 for bundling health care services into a health care service bundle indicator. Such standardized bundles of care may be considered a health care service bundle indicator, which is similar to a stock keeping unit (SKU), commonly used in inventory management to denote a specific item for sale. As described herein below, a health care service bundle indicator may comprise information regarding specific health care services as well as additional information that may inform the price of the health care service bundle indicator, such as region and specific provider. Thus method 200 particularly relates to the bundling of health care services informed by claims and other data and the representation of such bundles using health care service bundle indicators.

An e-commerce platform 201, such as the e-commerce platform 101 described herein above, may form and refine standardized bundles of health care services based on historic and current data. For example, the e-commerce platform 201 may obtain national claims information from a national claims database 202. In particular, the e-commerce platform may identify engagements of care from the data 202, which may be delivered to the e-commerce platform 201 in the form of, say, an Excel document. The e-commerce platform 201 may further obtain metadata from an internal e-commerce platform database 204, where such metadata may comprise, for example, order information, provider listings, fulfillment data, and CPT and ICD-9/10 data.

After identifying and refining bundles of services, the e-commerce platform 201 may generate an identifier, or health care service bundle indicator 206, for each bundle by applying a taxonomy to the bundle. In one example, a health care service bundle indicator taxonomy may comprise a service category, service group, service type, location, and single unit code, where the service category may correspond to a broad health care service category, the service group may correspond to a subset of services within the broad health care service category, the service type may correspond to a specific set of services within the group, the location may correspond to a geographical region or a health care practice where the service may be rendered, and the single unit code may encode additional information such as a specific provider.

The health care service bundle indicator taxonomy may enable a health care service bundle indicator to clearly identify a specific bundle of health care services so that health care providers may easily associate a price with a health care service bundle indicator and health consumers may easily understand what services are offered by a health care provider. For example, one component of a health care service bundle indicator taxonomy may comprise a health care service category. Examples of service categories may include, but are not limited to, primary care, imaging, therapy, vaccinations, dental, vision, hearing, labs, complementary and alternative medicine (CAM), and so on. Each service category may contain one or more health care service groups. For example, a primary care service category may include service groups such as wellness exams and minor illness or injury visits. An imaging service category may include service groups such as mammograms, x-rays, ultrasounds, and MRIs. A therapy service category may include service groups such as physical therapy, occupational therapy, and speech therapy. A vaccinations service category may include service groups such as flu shots, chicken pox, MMR, and Hepatitis A and B. A dental service category may include service groups such as exams and cleanings. A vision service category may include service groups such as eye exams, vision tests, and contact lens fittings. A CAM service category may include service groups such as chiropractic exams, acupuncture sessions, and massage sessions. As described further herein, each service group may include one or more bundles of health care services, or service types, related to the service group.

Thus a health care service bundle indicator comprises a specific bundle of health care services and may be denoted by a distinctive identifier. To form a distinctive health care service bundle indicator identifier, a code may be assigned to each category relating to the health care service bundle indicator. The format of a health care service bundle indicator may comprise any combination of codes according to a specified taxonomy that identifies a bundle of care. For example, each service group may be assigned a three-letter code and each service bundle may be assigned a two-digit code that is within the service group. A combination of a service group code and a service bundle code may form a product code, referring to a particular combination of health care services. Further, each location where a service can be delivered may further be assigned a three-letter code, and each provider who offers a service on the marketplace may be assigned a three-letter code. A health care service bundle indicator identifier may thus be constructed by concatenating the location code to the provider code and the product code.

In some examples, a health care service bundle indicator may represent a specific set of health care services offered by a specific provider. For example, within a preventative care category, a service group may comprise a wellness exam denoted by the three-letter code WEL. A particular service within the wellness exam service group may comprise a group of common procedure terminology (CPT) codes, for example "Men's Wellness Exam, Age 60-64, Established Patient, History of Increased Blood Pressure, With Screening Colonoscopy" may be the plain language equivalent of the CPT codes 99396, 82947, 80061, and 60121. This particular combination of services may be assigned a two-number code, for example 17. Therefore the product code for this service may be WEL17. As described hereinabove, a health care service bundle indicator may include such a product code in addition to codes identifying a specific provider. For example, a provider location code for the NW Doctors Group located at 1234 SW Market Street in Portland, Oreg. may be denoted by NWD, while a provider code for a specific health care provider, say Dr. John Doe, working at the provider location may be denoted by the three-letter code JDO. Therefore the health care service bundle indicator for the specific preventative care service bundle described above offered by Dr. John Doe at the NW Doctors Group may be NWDJDOWEL17.

As another example, a service group within an imaging category may comprise a mammogram denoted by the three-letter code MAM. A particular service within this service group may comprise a group of CPT codes, for example "Screening mammography producing direct digital image plus computer aided detection" may be the plain language equivalent of the CPT codes 60202 and 77052. This particular combination of services may be assigned a two-number code, for example 02. Therefore the product code for this particular bundle of services may be MAM02. A particular provider location, for example the PDX Imaging Center at 5555 Hawthorne Boulevard in Portland, Oreg., may be a three-letter code, for example PIC. A particular provider working at the particular provider location, say Dr. Jane Smith, may be assigned a three-letter code, for example JAS. Therefore the health care service bundle indicator for the specific imaging service bundle described above offered by Dr. Jane Smith at the PDX Imaging Center may be PICJASMAM02.

As yet another example, a service group within a primary care category may comprise an illness or injury visit denoted by the three-letter code NNV. A particular service within this service group may comprise a group of CPT codes, for example "Sore throat/possible strep throat—established patient" may be the plain language equivalent of the CPT codes 99213 and 87880. This particular combination of services may be assigned a two-number code, for example 04. Therefore the product code for this particular bundle of services may be NNV04. A particular provider location, for example Doctor Now at 7 Division Street in Portland, Oreg., may be a three-letter code, for example DNW. A particular provider working at the particular provider location, say Dr. Melissa Jones, may be assigned a three-letter code, for example MJS. Therefore the health care service bundle indicator for the specific primary care service bundle described above offered by Dr. Melissa Jones at Doctor Now may be DNWMJSNNV04.

As another example, a service group within a primary care category may comprise an illness or injury visit denoted by the three-letter code NNV. A particular service within this service group may comprise a group of CPT codes, for example "Minor condition office visit, new patient" may be the plain language equivalent of the CPT code 99203. This particular combination of services may be assigned a two-number code, for example 01. Therefore the product code for this particular bundle of services may be NNV01. A particular provider location, for example Doctor Now at 7

Division Street in Portland, Oreg., may be a three-letter code, for example DNW. A particular provider working at the particular provider location, say Dr. James Robinson, may be assigned a three-letter code, for example DJR. Therefore the health care service bundle indicator for the specific illness or injury visit service bundle described above offered by Dr. James Robinson at Doctor Now may be DNWDJRNNV01.

As yet another example, a health care service bundle indicator may comprise a sequence of alphanumerical characters following the pattern XXX-XXXX-XXX. For example, the first segment of the sequence (i.e., the three characters before the first dash) may refer to a service bundle, wherein a specific combination of alphanumeric characters refers to a specific combination of CPT codes. The second segment of the sequence (i.e., the four characters after the first dash and before the second dash) may refer to a provider, wherein a specific combination of alphanumeric characters refers to a specific provider of the service bundle. The second segment may further refer to an applicable provider network. For example, a doctor may be contracted for price A for a particular service under an HSA plan, but may also be contracted for price B for the same particular service under a copay plan. Thus, the second segment may include additional information related to the provider in order to correctly identify the contracted price for a service. The third segment of the sequence (i.e., the three characters after the second dash) may refer to a location. In some examples, the sequence of the third segment may have a specified relation to the geographic market. However, in other examples, the sequence of the third segment may be system generated; for example, the sequence may be based on the order in which a location is set up in the e-commerce platform. The list of valid alphanumeric characters may include 0-9 and A-Z. In some examples, the list of valid alphanumeric characters may be a subset of the aforementioned list for the purpose of distinguishability. For example, the list of valid alphanumeric characters may include 2-9 and A-Z (excluding "0") in order to exclude 0, 1, and 0 because 0 and 0 may be difficult to distinguish and 1 and I may be difficult to distinguish. The alphanumeric characters may further be ordered such that the lowest value character is 2, for example, and the highest value character is Z. Thus the lowest possible health care service bundle indicator may be 222-2222-222, while the highest possible health care service bundle indicator may be ZZZ-ZZZZ-ZZZ. Furthermore, the number of characters and segments may vary. For example, the health care service bundle indicator may include more than three segments in the sequence, and each sequence may include any suitable number of characters to uniquely identify a service bundle offered by a provider in a geographical region.

Thus any taxonomy capable of uniquely identifying a bundle of care may be utilized to construct a unique identifier of a health care service bundle indicator. As described above, one taxonomy may specify a particular bundle of care delivered in a geographical region, while another taxonomy may specify a particular bundle of care delivered by a specific provider.

Bundling a set of health care services into a product code allows providers to set a price for a product code—thereby generating a health care service bundle indicator—and allows health care consumers to search for health care services by product code and compare the health care service bundle indicators associated with each provider. By encouraging providers to offer a specific bundles of health care services associated with specific product codes, consumers may experience consistency among providers when shopping for health care services and prices.

FIG. 2B shows a high-level diagram illustrating an example method 220 for bundling health care services into a health care service bundle indicator. In particular, method 220 relates to the automatic generation of receipt documentation and a health care claim from a purchased bundle of care. A provider bundle 226 may be formed based on a plurality of CPT codes 222 most often added to health care services and a taxonomy 224, such as the taxonomy described herein above. The provider bundle 226 may therefore comprise a standard service 227 which may comprise a plurality of CPT codes, for example CPT code A, CPT code B, and CPT code C. The provider bundle 226 may include additional CPT codes, such as CPT code D and CPT code F, in addition to the standard service 227. These additional CPT codes may be selected, as non-limiting examples, by the provider and/or the consumer, or may be selected based on the taxonomy 224. The provider bundle 226 may comprise and/or may be represented by a health care service bundle indicator which uniquely identifies the provider bundle.

A health care consumer may purchase the provider bundle 226 from a particular provider in a single order 230. Thus the single order 230 may comprise the purchased service (i.e., the provider bundle 226), user information identifying the health care consumer, and provider information identifying the particular provider. The provider information may further include information identifying an applicable provider network, so that the price of the health bundle offered to a consumers in the e-commerce marketplace may vary based on which network the provider is contracted with since individual health plans are affiliated with specific provider networks.

Based on the single order information, the e-commerce platform may generate receipt documentation 232 for the consumer, where the receipt documentation 232 comprises purchased service information (e.g., a description of the service in non-technical terms), provider information, and user information. Additionally, a claim 234 may be generated based on the single order 230 after fulfillment of the order. The claim 234 may include a technical description of the services provided in a standardized format. For example, the claim 234 may include a plurality of CPT codes associated with the provided services, additional medical classifications (e.g., ICD-10), user insurance information, and provider information.

Figure 3A:
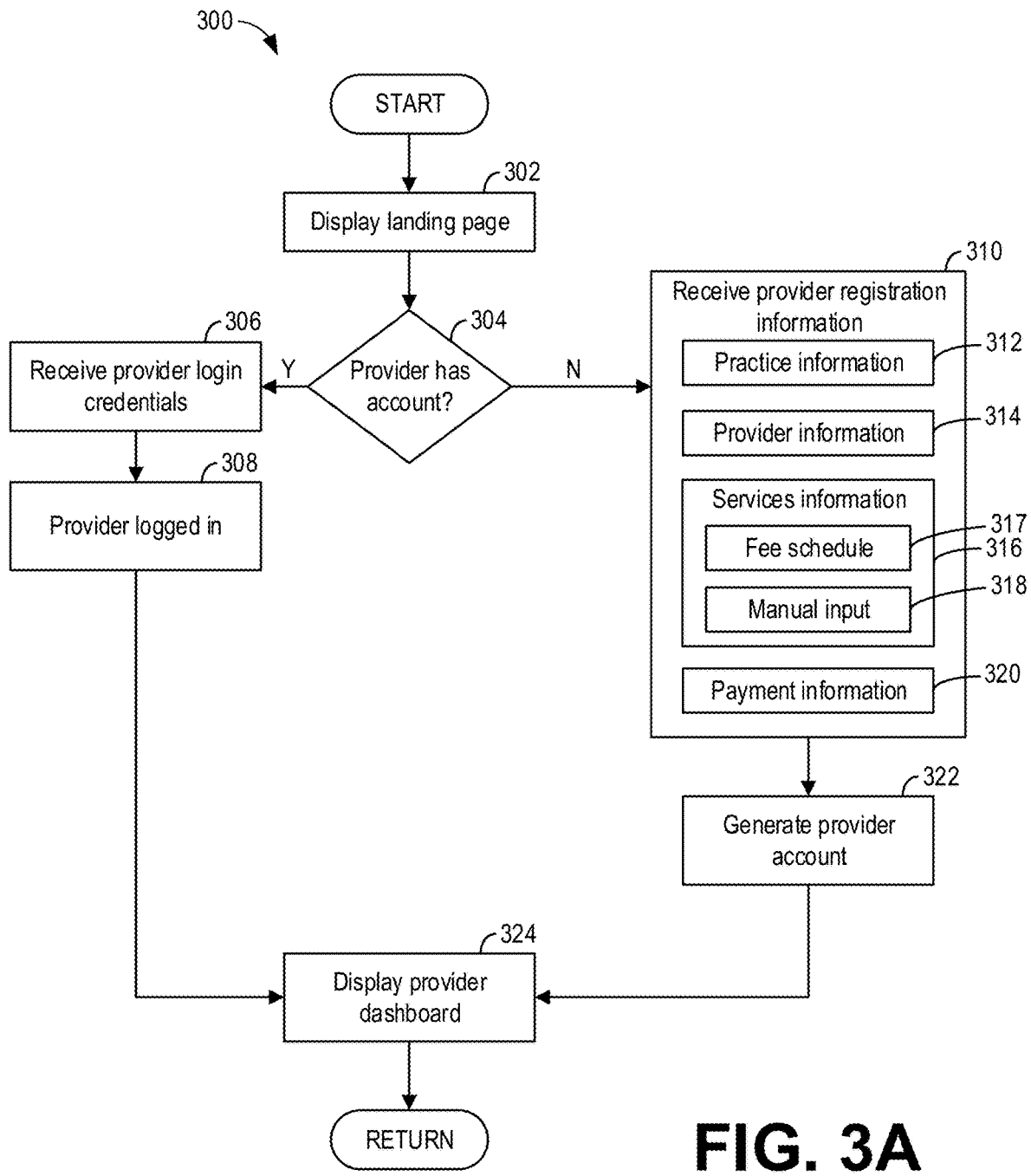
FIGS. 3A-3C show high-level flow charts illustrating example methods for a health care provider using an e-commerce health care platform.

FIG. 3A shows a high-level flow chart illustrating an example method 300 for enrolling a health care provider into an e-commerce health care platform. The method will be described herein with reference to the systems and components depicted in FIGS. 1A-1D, however it should be appreciated that the method may be carried out by other systems and components without departing from the scope of the disclosure.

Method 300 begins at 302, when a provider connects to the e-commerce platform. At 302, the e-commerce platform 302 may provide, to a computing device of the provider, a provider-specific landing page for display to the provider.

At 304, the method includes determining if the provider has an account with the e-commerce platform. If the provider has an account ("Y"), method 300 proceeds to 306 where the e-commerce platform receives login credentials for the provider. If the login credentials are valid, the provider is logged into the provider account at 308. Once logged in, the e-commerce platform may provide a provider dashboard for display to the provider, wherein the provider dashboard includes functionality for a provider to view orders, confirm fulfillment of orders, view incoming and/or settled payments, and so on. The method may then end.

Returning to 304, if the provider does not have an account with the e-commerce platform ("N"), method 300 proceeds to 310. At 310, the e-commerce platform receives provider registration information. Provider registration information may include practice information 312 comprising details regarding the provider's practice (e.g., a clinic, hospital, and so on), and provider information 314 comprising details regarding the provider. The provider registration information may further include services information 316 comprising details regarding which services the provider will offer on the e-commerce platform. As described further herein, the provider may upload a fee schedule 317 which includes fees for select services, which may be automatically processed by the e-commerce platform. Additionally or alternatively, the provider may provide manual input 318 regarding the services. Provider registration information may further include payment information 320 comprising, for example, details regarding a financial account of the provider into which funds may be transferred for services provided.

At 322, the e-commerce platform generates a provider account based on the received provider registration information. After generating the provider account, at 324 the e-commerce platform may provide a provider dashboard for display to the provider. The method may then end.

Figure 3B:
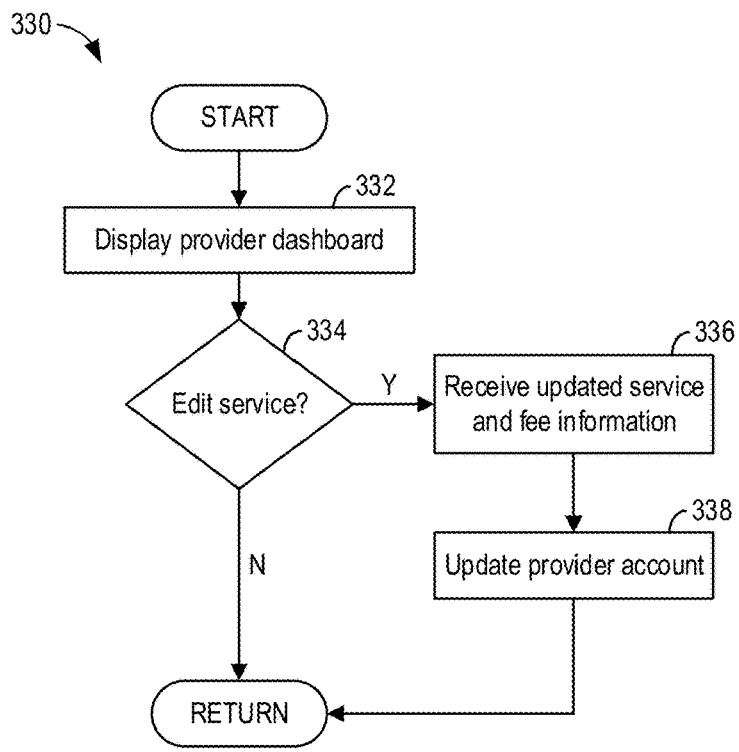

FIG. 3B shows a high-level flow chart illustrating an example method 330 for adjusting fees for health care services. As described further herein, a provider may adjust fees for particular services offered on the e-commerce platform at any time. The method will be described herein with reference to the systems and components depicted in FIGS. 1A-1D, however it should be appreciated that the method may be carried out by other systems and components without departing from the scope of the disclosure.

Method 330 begins at 332, wherein the e-commerce platform displays a provider dashboard to the provider. At 334, the method includes determining if the provider is attempting to edit service information. If the provider is not attempting to edit service information ("N"), then the method ends. However, if the provider is attempting to edit service information ("Y"), method 330 proceeds to 336. At 336, the e-commerce platform receives updated service and fee information. At 338, the e-commerce platform updates the provider account with the updated service and fee information. The method then ends.

Figure 3C:
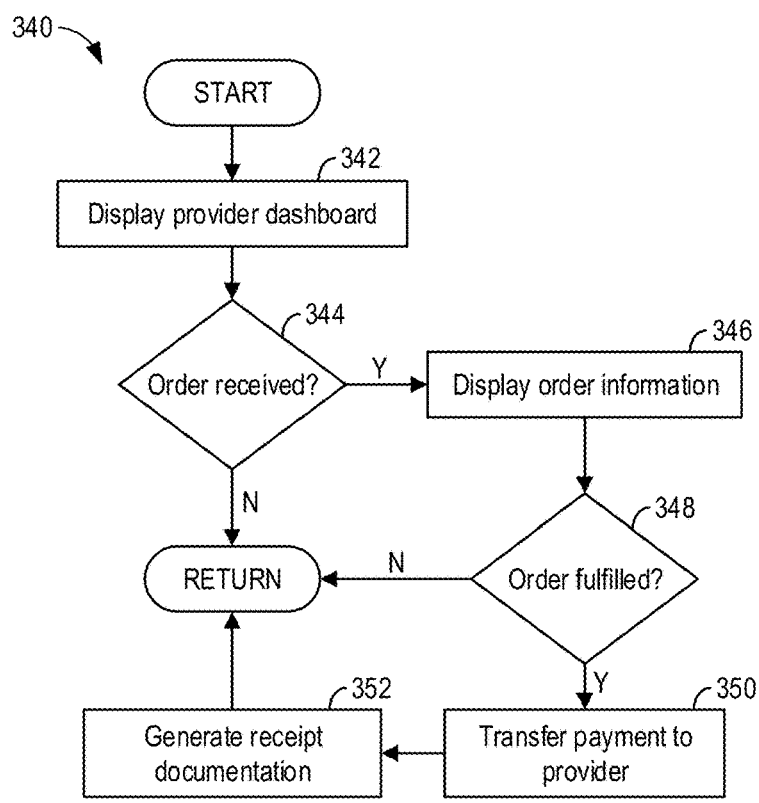
Figure 4A:
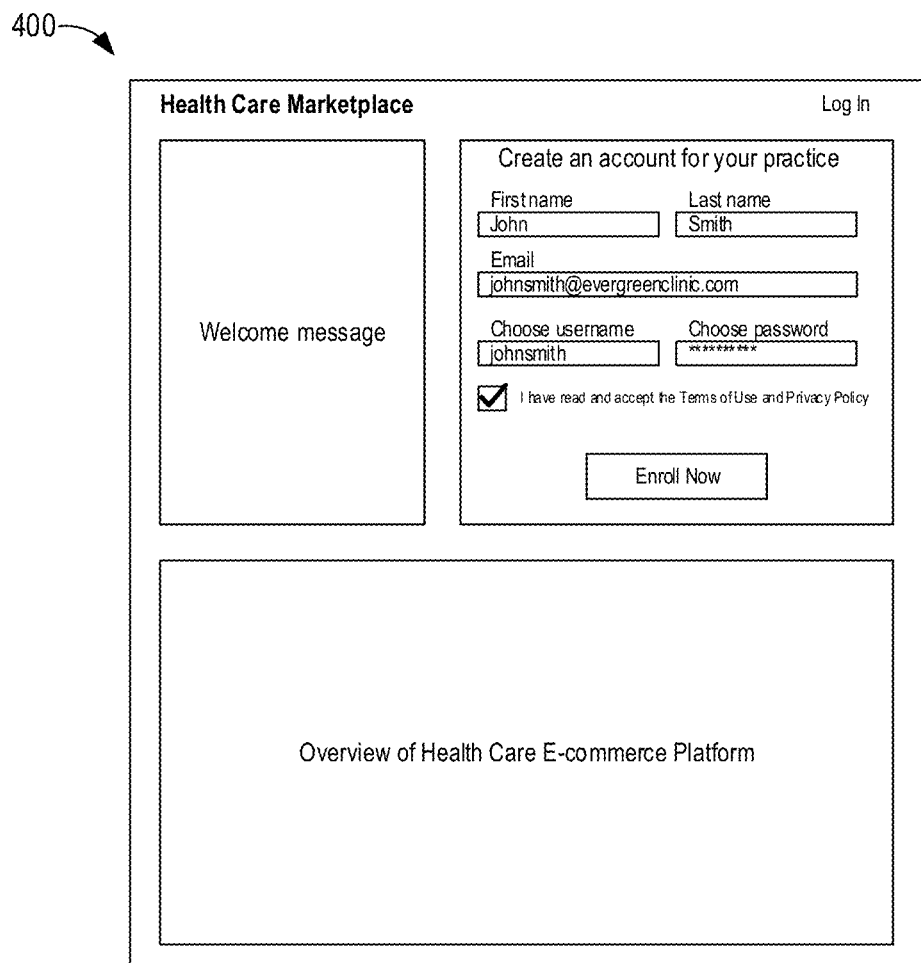

FIG. 3C shows a high-level flow chart illustrating an example method 340 for facilitating reporting of fulfilled services and payment for said services. The method will be described herein with reference to the systems and components depicted in FIGS. 1A-1D, however it should be appreciated that the method may be carried out by other systems and components without departing from the scope of the disclosure.

Method 340 begins at 342, wherein the provider dashboard is displayed to the provider. At 344, the method includes determining if an order for a health care service is received. If no order is received ("N"), the method ends. However, if an order is received ("Y"), then the order information is displayed to the provider at 346. At 348, the method includes determining if the order is fulfilled. The provider is responsible for confirming via the e-commerce platform that the order is fulfilled (i.e., that the provider has provided the services purchased by a consumer to the consumer). If the order is not fulfilled ("N"), then the method ends. However, if the order is fulfilled ("Y"), then method 340 proceeds to 350. At 350, the e-commerce platform facilitates the transfer of a payment to the provider. The payment may include the out-of-pocket cost paid by the consumer in addition to costs covered by a health care plan of the consumer. At 352, the e-commerce platform may generate receipt documentation to be provided to the consumer, as well as claim documentation to be provided to an administrator of the health care plan, a clearinghouse, and so on. Method 340 then ends.

FIGS. 4A-4F illustrate example e-commerce health care platform interfaces for a health care provider. In particular, interface 400 in FIG. 4A comprises a landing page for a health care provider. Interface 400 includes a brief registration form and an overview of how the e-commerce platform marketplace functions.

After a provider fills out the registration form, a second interface is shown to the provider. The second interface includes a specific overview of the information necessary to complete a provider account profile, such as practice basics, office locations, providers, payment preference, and services. The second interface further allows the provider to add a colleague to the registration process to assist with setting up the account.

A third interface includes a form for practice information. The form may comprise inputs for a plurality of details regarding the practice, including a legal business name, a practice name, a business tax identification number, an organization national provider identification (NPI) number, an address, contact information, and authorized personnel of the practice other than the provider who may use the e-commerce platform.

A fourth interface includes a form for provider information. The form may comprise inputs for a plurality of details regarding the provider, including name, gender, languages spoken, credentials, specialties, provider NPI number, and a biography.

After the provider enters information about the practice where he or she works, the location(s) of the practice, and the providers who work at the practice including the provider setting up the account, the provider may set up the at least one service that the provider plans to sell through the e-commerce platform. A fifth interface shows multiple options for setting up at least one health care service, including uploading a fee schedule, and a manual setup tool. In some examples, one option may include a guided walkthrough wherein a representative of the e-commerce platform assists the provider, for example via a co-browsing session, in setting up a service catalog.

Via a sixth interface, uploading a fee schedule in order to set up a service may comprise uploading a file containing the provider's fee schedule for health care services. The sixth interface may allow a provider to upload a fee schedule in any format, such as PDF, DOCX, XLSX, CSV, TXT, or an image file. The e-commerce platform uses the uploaded fee schedule to form a draft of a service catalog for the provider, which may later be edited and approved by the provider prior to displaying the services in the e-commerce platform marketplace. The sixth interface may further include registration information previously entered by the provider, including but not limited to the practice information and provider information.

After setting up the services information, the provider may be prompted to input payment account information, for example via a seventh interface. The seventh interface includes a form for payment account information, which may include at least a tax identification number. In some examples, the e-commerce platform may retrieve specific account details based on the tax identification number. In other examples, the seventh interface may further include inputs for specific account details.

After setting up the payment account information, a provider account may be generated based on the information provided by the provider, and the provider may be shown an eighth interface. The eighth interface may include a notice indicating that the account is successfully established, as well as an application summary comprising all of the information input by the provider.

If the provider opts to manually input service information as discussed above instead of uploading a fee schedule, the provider may be shown a ninth interface. The ninth interface includes a setup tool comprising one or more drop-down menus containing selectable information. For example, the setup tool may include a category drop-down menu and a service type drop-down menu so that the provider may setup a particular service to offer through the e-commerce platform.

Once the provider selects a category and a service type, the e-commerce platform may display a default list of procedures associated with the particular category/service type combination, via a tenth interface. For example, as shown in interface 415 in FIG. 4B, the provider may select a price or fee for each category/service type combination (i.e., for each health care service bundle indicator). Interface 415 may display the average regional price for each bundle of procedures. Additionally or alternatively, interface 415 may display the average contracted rate for providers in the region or simply the contracted rate/negotiated fee schedule with that provider (taking into account different network affiliations). In this way, the provider may select a fee for a specific product code in order to compete with other providers. In some examples, the provider may be required to offer a particular list of procedures in order to qualify for an e-commerce platform account.

As described herein above with regard to FIG. 3B, the provider is not limited to offering the services at the fees established when setting up the account. As depicted in interface 430 of FIG. 4C, the provider may adjust prices for each health care service bundle indicator by adjusting the price for a specific procedure or CPT code, or by adjusting the price for a bundle of procedures. In particular, interface 430 illustrates how after a provider is enrolled in the e-commerce platform, the provider may adjust the price of a product code, or bundle of health care services, offered at any time. Interface 430 displays a list of the product codes offered by the provider, the price for each product code set by the provider, and a comparison to the average regional price for each product code. The provider may easily edit the price of a product code via interface 430. The provider may decide to charge the average regional price for a particular product code, or may decide to charge less than the average regional price. As another example, the provider may choose to lower the price for new patient visits in order to entice consumers to purchase the provider's health care service bundle indicator. In this way, the price for each product code is at the discretion of the provider, which may be influenced by competition in the marketplace or by personal factors such as workload rather than contractual agreements or arbitrary decisions. As a result of providers being able to view the average price of a product code as well as the prices offered by competing providers when adjusting the price of a product code, the costs of health care services may be lowered throughout the health care marketplace.

Thus, systems and methods are provided for enrolling a health care provider into an e-commerce platform for selling health care services in convenient pre-bundled packages. In some examples, the provider may provide information regarding a health care practice and about other providers working at the same health care practice, such as location, name, contact information, office hours, and so on. Further, the provider may use various methods to upload the health care services that the provider offers. For example, the provider may upload a fee schedule containing information about health care services offered and associated fees, and this information may be automatically input by the e-commerce platform or may be manually input by an e-commerce platform representative. As another example, the provider may use a setup tool to input health care services offered and input prices. As yet another example, the provider may contact an e-commerce platform representative, who may then guide the provider through the setup process. The provider may input all health care services offered upon enrollment, or may input at least one health care service upon enrollment and input additional health care services offered at a later time. When the provider is inputting health care services offered and the associated price, the e-commerce platform may display an average regional price for a health care service. In this way, the provider may understand the market value of a health care service, and may accordingly set a price based on the average regional price displayed. In some examples, the e-commerce platform may provide a list of health care services that the provider must offer to be eligible to use the e-commerce platform. This list of health care services may comprise the most common health care services offered by other health care providers. In this way, the e-commerce platform may encourage consistency for health care services offered by health care providers using the e-commerce platform.

FIG. 4D shows an example interface 445 for a provider to view purchased orders. Interface 445 includes a list of orders placed by health care consumers for health care services to be provided by the provider. When the provider has fulfilled an order, the provider may select an order from the list of orders to indicate that the order is fulfilled. When an order is selected, the provider may be shown an interface such as interface 460 in FIG. 4E, wherein the provider may input details such as the date of service, an invoice number, an account number, procedure codes for services provided, a quantity of the services provided, diagnosis codes, and so on. Once the provider enters the order fulfillment information, the provider may receive payment for the provided services. Thus, interface 460 may include a button to submit the order, wherein the button indicates that the provider will get paid upon submission. Once the provider selects the button, the e-commerce platform processes the order fulfillment and provides an interface such as interface 475 in FIG. 4F. Interface 475 displays confirmation of a fulfilled order, and thus includes information regarding the order such as an order identification number, an order date, a status, a provider fee, a processing fee, a net amount paid to the provider, a service date, a submission date, a payment date, an invoice number, an account number, and procedure and diagnosis codes for the provided services. The information regarding the order may further include patient details, service details, provider details, and so on. Interface 475 may further indicate to the provider that the provider does not need to submit a claim for the provided services, as the e-commerce platform performs this function instead.

Thus, the e-commerce platform provides a plurality of user interfaces for a health care provider to interact with the e-commerce platform. Via these user interfaces, which may be displayed using a computing system of the provider, the provider may enroll in the e-commerce platform, select health care services to offer via the e-commerce platform, establish fees for the selected health care services, edit the fees at any time, and manage orders placed by health care consumers.

As described further herein with regard to FIGS. 5-6L, the e-commerce platform further provides methods and interfaces for health care consumers.

FIG. 5 shows a high-level flow chart illustrating an example method 500 for a health care consumer on an e-commerce health care platform. In particular, method 500 relates to how the e-commerce platform may interact with a health care consumer. Method 500 may be carried out, as a non-limiting example, by the e-commerce platform 101 described herein above with regard to FIGS. 1A-1D, though it should be understood that the method may be carried out by other systems without departing from the scope of the current disclosure.

Method 500 begins at 505, when a health care consumer or user connects to the e-commerce platform. At 505, method 500 includes displaying a landing page. The landing page may, for example, resemble the user interface 600 described herein below with regard to FIG. 6A, and may provide form inputs for the user to enroll in an e-commerce marketplace or login to the e-commerce marketplace.

At 510, method 500 includes determining if the user has an e-commerce platform account. If the user has an e-commerce platform account ("Y"), method 500 proceeds to 515. At 515, method 500 includes receiving the user login credentials, which may comprise, as non-limiting examples, a user name and a password. Method 500 then proceeds to 535.

However, if the user does not have an e-commerce platform account ("N"), method 500 proceeds from 510 to 520. At 520, method 500 includes receiving registration information. Registration information may include biographical details of the user, health care benefits plan information for the user, financial information for the user, and so on.

At 525, method 500 includes generating a user account. The user account may be generated based on the received registration information. At 530, method 500 includes linking a health care plan to the user account. Specifically, the health care plan may be linked to the user account based on the health care benefits plan information included with the received registration information. Linking the health care plan to the user account comprises performing an eligibility confirmation with, as a non-limiting example, an insurance administrator of the health care plan. That is, the e-commerce platform may submit an eligibility verification request to the insurance administrator regarding whether the user is eligible for health care coverage and if so, the details of coverage such as which services are covered, deductible information, and so on. The insurance administrator verifies the eligibility of the user, and information received from the insurance administrator is stored in the e-commerce platform so that further eligibility verification may not be performed.

At 535, method 500 includes displaying a health care storefront. The health care storefront may include a search tool which enables the user to search for health care services and providers based on geographic location. An example user interface for a health care storefront is described further herein with regard to FIG. 6B.

At 540, method 500 includes receiving a query. The query may comprise a health care service or provider and a geographic location input to the search tool by the user. At 545, method 500 includes retrieving and displaying query results. The e-commerce platform searches one or more databases for the queried health care services and/or providers based on the geographic location. Search or query results may then be displayed to the user. The query results may comprise a list of providers offering the health care services in the geographic location. Additionally or alternatively, the query results may comprise a list of health care services offered by a queried provider. The user may then select a particular combination of health care services and a provider, and place an order for the particular combination. Such a combination may be represented in the e-commerce platform by a health care services bundle indicator which uniquely identifies the combination of health care services and provider. As described further herein, the query results may further include a cost breakdown of the health care services based on fees provided by the health care providers as well as a health care benefits plan of the user.

After the user places an order, at 550, method 500 includes receiving an order. At 555, method 500 includes receiving payment. Payment for the order may comprise an out-of-pocket cost to the user calculated based on the provider fee and the health care benefits plan of the user. The out-of-pocket cost may further be calculated based on a deductible of the user. The payment may be automatically withdrawn from a financial account of the user. Method 500 then ends.

FIGS. 6A-6L illustrate example e-commerce health care platform interfaces for a health care consumer. Notably, the example interfaces for a consumer illustrated in FIGS. 6A-6L are functionally different from the example interfaces for a provider illustrated in FIGS. 4A-4F.

Figure 6A:
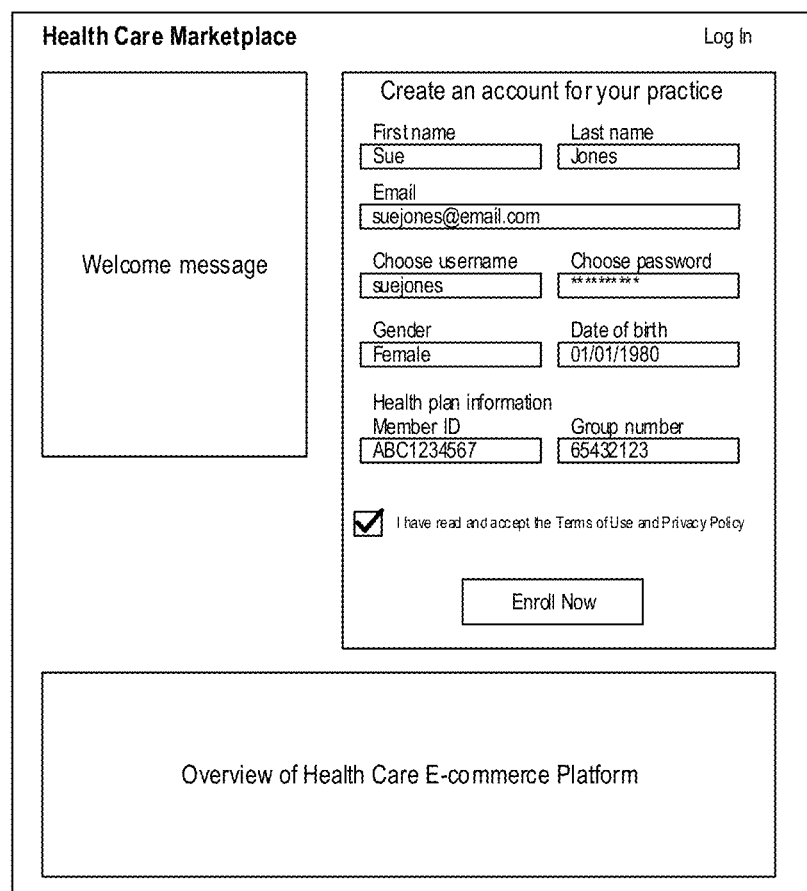

FIG. 6A includes an interface 600 comprising a landing page for a health care consumer. Interface 600 includes a brief registration form, a login form, and an overview of the e-commerce platform features for a health care consumer. In some examples, the e-commerce platform may be available to a health care consumer through a health care plan offered by an employer of the health care consumer. In such examples, the registration form may require information identifying the health care consumer as an employee of the employer. In some examples, such as that depicted in interface 600, the registration form may include form inputs for a health care plan of the consumer so that the health care benefits plan may be linked to an account of the consumer. For example, the form may include inputs for name, gender, date of birth, contact information, health care plan member identification number, health care plan group number, and so on. As described herein, the e-commerce platform may use the health care consumer's health care benefits plan information to determine eligibility for services as well as compute out-of-pocket costs for the consumer based on the benefits.

In some examples, the health care consumer may register for an account using interface 600. As shown, interface 600 includes form inputs for a user account, including but not limited to user name, password, and contact information.

After registering and/or logging into the e-commerce platform, the health care consumer may be shown an interface including an account creation confirmation to acknowledge the successful creation of a user account.

FIG. 6B shows an example interface 608 that comprises an e-commerce platform storefront. As such, interface 608 may include, but is not limited to, a search function for finding health care services and providers, a link to obtain assistance with the e-commerce platform, a link to connect to a telehealth system so that the health care consumer may communicate with a health care professional over a secure video or phone line, a link to associate the account with the health care consumer's health plan, health savings account (HSA), or health reimbursement account (HRA), and so on.

Figure 6C:
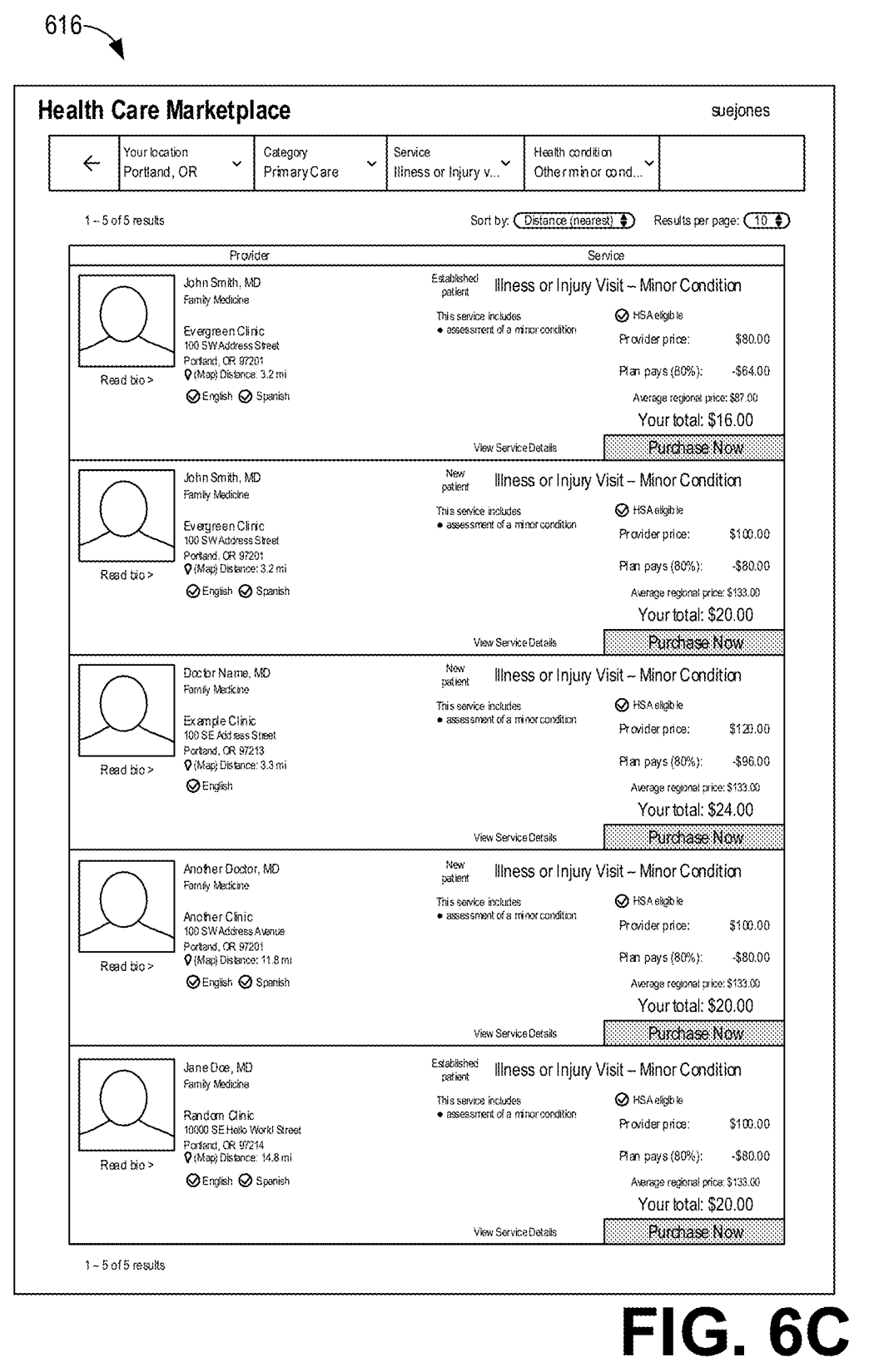

After a health care consumer places a query, say for a specific type of illness or health care service desired, using the search tool shown in interface 608 of FIG. 6B, interface 616 in FIG. 6C may be displayed. For example, interface 608 may comprise a health care consumer's e-commerce platform account home page, and illustrates how a consumer may utilize the search function by entering a desired health care service type and location information, such as a zip code or city. After entering search criteria and clicking the search button, the e-commerce platform retrieves results based on the search criteria. Interface 616 shows one example of how search results may be displayed to a health care consumer. The search results comprise a list of providers who provide the health care service that the consumer searched in the geographic location included in the query. Each result may include information such as the price for the service offered by the provider, a quality rating of the provider based on input from other health care consumers, information regarding the provider, and a comparison of the price offered by the provider to the average regional price. The price for the service offered by the provider may comprise an out-of-pocket cost to the consumer, which the e-commerce platform may determine based on, as non-limiting examples, the consumer's health care plan (e.g., deductible, contract rates, etc.), the applicable provider network, the fees established by the particular provider, and so on. As discussed above, each of the services and corresponding fees for each provider in the search results may be associated with a health care service bundle indicator that uniquely identifies the combination of service and provider.

The health care consumer may view more information regarding the search results. For example, an additional interface may show a provider page which includes, as non-limiting examples, the name of the provider, a photograph of the provider, provider credentials, languages spoken, gender, practice location, services offered (including, as depicted, fee information for each service), user ratings, insurance status, and a biography of the provider.

Additionally or alternatively, the health care consumer may view more information regarding a specific service offered by a particular provider. For example, a separate interface may include a service summary for a selected health care service bundle. Said interface may display pricing information for the selected health care service bundle, such as the provider price, an amount paid by the health care plan of the health care consumer, and the out-of-pocket cost. Said interface may further display an average regional price for the selected health care service bundle. Said interface may also display provider details and practice details.

The interface may also include a "Purchase Now" button which enables the health care consumer to purchase the selected health care service bundle for the listed out-of-pocket cost. For example, if the health care consumer selects the "Purchase Now" button, the e-commerce platform may provide interface 624 in FIG. 6D to the consumer. Interface 624 includes an order overview of the selected health care service bundle. Interface 624 may include form inputs so that the consumer may identify who will be receiving the service. The consumer may also optionally select, via interface 624, whether or not the e-commerce platform will submit a claim for the service on behalf of the consumer. If the consumer declines to allow the e-commerce platform to submit a claim, then the consumer may be responsible for 100% of the provider price and the payment may not be applied to the consumer's deductible unless the consumer submits a claim.

Interface 624 may further include a cost breakdown for the selected service bundle, including the provider price, the amount covered by the health care plan, and the out-of-pocket cost to the consumer. Interface 624 may also display a co-insurance payment, for example. The consumer may select to cancel the order for the selected service or may proceed to payment. As depicted in interface 624, the consumer has not met a health care plan deductible and thus has a non-zero out-of-pocket cost.

As another example, interface 632 in FIG. 6E shows an order overview for a selected health care bundle wherein the health care plan does not cover the selected service. Thus, the cost breakdown indicates that the plan does not contribute to the cost of the service, so that the out-of-pocket cost to the consumer equals the full price of the service as established by the provider.

As yet another example, interface 640 in FIG. 6F shows an order overview for a selected health care bundle when the consumer has met a health care plan deductible. In this case, the health care plan covers the full cost of the selected service, and the out-of-pocket cost to the consumer is zero. Thus, the e-commerce platform may determine an out-of-pocket cost based on the health care benefits plan of the consumer, taking into account a deductible, so that the consumer may know prior to receiving the service how much the service will personally cost. This function of the e-commerce platform provides a distinct advantage over previous methods and systems for purchasing health care services, wherein a consumer often does not know how much he or she will pay out-of-pocket for any given health care service until after the health care service is provided.

Thus, the e-commerce platform may obtain detailed benefits information from a consumer's health care plan and apply such benefits information to a cost to a consumer for a health care service bundle indicator at the point of purchase. Furthermore, this information may be clearly displayed to a health care consumer at the point of purchase so that he or she may understand the coverage received and the amount due out-of-pocket.

Figure 6G:

If the health care consumer chooses to proceed with payment for a selected service, interface 648 in FIG. 6G may be displayed to the consumer. Interface 648 includes form inputs that enable the consumer to select a payment option. As depicted, payment options may include, but are not limited to, an HSA card or any suitable debit/credit card. Interface 648 may further include form inputs to select a billing address. Interface 648 may further include an order overview as described above.

After selecting a payment option, the health care consumer may select a button to securely submit payment for the health care service bundle. If the button is selected, the e-commerce platform processes the payment (or alternatively, coordinates with a payment processor to securely process the payment) which comprises the out-of-pocket cost to the consumer. Interface 656 in FIG. 6H may then be displayed to the consumer. Interface 656 includes an order confirmation for the purchased service bundle, and may include an order identification number, date of purchase, information regarding the service purchased, the out-of-pocket cost paid for the service, a cost breakdown, and information regarding how to schedule an appointment with the provider for the purchased service bundle. Assistance may be offered for setting up an appointment through the e-commerce platform. For example, a telephone hotline or messaging service may be provided by interface 656 for the consumer to contact a representative for the e-commerce platform who may assist the consumer in arranging the appointment.

After purchasing a service bundle, the health care consumer may view purchased orders, for example, via interface 664 of FIG. 6I. Interface 664 includes an overview of order history so that the consumer may have a record of purchased services. Interface 664 may also include a status of each order, wherein the status indicates whether the service has been fulfilled.

After placing an order for a health care service bundle, the consumer schedules an appointment with the provider, visits the provider, and receives the purchased service. When visiting the provider, the consumer does not need to pay because the out-of-pocket costs to the consumer were purchased in advance. After the order is fulfilled, the consumer receives receipt documentation regarding the fulfilled service. Interface 672 in FIG. 6J shows example receipt documentation. In particular, the receipt documentation may include a plurality of information regarding the fulfilled order, including but not limited to member (consumer) information, health plan information, a payment summary, customer transactions (e.g., payments by the consumer), a service summary, patient details, provider details, claim information (e.g., procedure codes, procedure summaries, diagnoses, etc.), and so on. In some examples, the receipt documentation may further include a description of the services in user-friendly language.

Figure 6K:
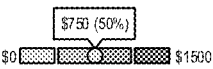

As discussed above, in some examples the health care consumer may link HSA/HRA account information with the e-commerce platform account. Interface 680 in FIG. 6K shows an example account overview, including information regarding linked plans such as health plan information and HSA/HRA account information. Interface 680 further includes a visual indicator of progress towards a deductible and transaction history.

Interface 680 in FIG. 6K allows a health care consumer to manage the e-commerce platform account for the consumer. To that end, interface 680 may include information regarding the user account, as well as information regarding the health care benefits plan. The health care benefits plan information may be automatically retrieved from, for example, a third-party administrator of the health care benefits plan, rather than the consumer. For example, interface 680 may display information from the linked accounts and displays relevant information regarding the accounts. For example, if the consumer links a health care plan to the e-commerce platform account, interface 680 may display an overview of the health care plan as well as progress towards a deductible. Further, interface 680 may include forms for linking the consumer's existing health plan and HSA/HRA to the consumer's e-commerce platform account. If the consumer links an HSA or HRA to the e-commerce platform account, interface 680 may display an overview of the HSA and/or HRA, including balance information and contribution information. In this way, a health care consumer may easily access information regarding his or her health care accounts. In some examples, interface 680 may further display an e-commerce platform transaction history, which may include previous orders applied to one of the consumer's health care accounts.

In some examples, the e-commerce platform may provide additional interfaces that include advanced search functions for refining the search results. For example, a health care consumer may refine the search by limiting the results to providers in the network, providers out of the network, providers that may accept HSA payment, and so on. Search results may be further refined by price range, distance, quality rating, and so on. The search result interfaces may further display information from the consumer's linked health care accounts so that the consumer may have information such as deductible and account balance on hand when choosing a particular health care provider. The prices displayed may take the consumer's health care plan deductible into account, so that the prices displayed comprise the out-of-pocket cost to the consumer.

Each search result interface may further include an option to compare search results, or providers. For example, if three search results appeal to a health care consumer, the consumer may select the three results for comparison. Interface 688 shown in FIG. 6L includes a comparison of providers selected via the search results interface. Detailed information regarding each provider may be displayed side-by-side for easy comparison, such as the price, how long each provider may take to provide the service, the distance of the provider from the consumer, the quality rating based on patient reviews, the specialty of the provider, the languages spoken by the provider, the hours that the provider is available, and so on. Interface 688 may further include options to immediately add a service from a particular provider to the consumer's e-commerce shopping cart.

As described hereinabove, a health care consumer may link his or her health care plan and/or HSA/HRA accounts to his or her e-commerce platform account. In this way, when a health care consumer purchases a health care service bundle indicator on the e-commerce platform, the up-front out-of-pocket price of the health care service bundle indicator may be based on the health care plan coverage and the consumer may use HSA/HRA funds to purchase the health care service bundle indicator.

Thus, a method for an e-commerce platform begins when a care seeker, or health care consumer, submits an order for a health care service bundle indicator. After submitting an order, the health care consumer may simply visit a clinic if the clinic is a walk-in clinic, or may make an appointment to visit a non-walk-in clinic. To make an appointment, the health care consumer may either contact the provider directly to schedule an appointment, or may contact an e-commerce platform representative who may assist in scheduling the appointment. Once the appointment is scheduled, the health care consumer visits the clinic at the appointed time. Note that all actions relevant to the health care consumer are grouped within a box.

In some examples, if the consumer decides to cancel the order prior to the appointment, the consumer may log in to the e-commerce platform and cancel the order. The order may be cancelled immediately by the e-commerce platform and the payment refunded to the consumer without any fees or penalties imposed for doing so. In examples where the consumer has already made an appointment with a provider, the consumer is responsible for contacting the provider to cancel the appointment.

Once the health care consumer is at the clinic, the provider at the clinic delivers the purchased service to the health care consumer. After the service is delivered, the method is directed towards the provider billing cycle. The provider logs in to the e-commerce platform. Once the provider is logged into the e-commerce platform, the provider opens the purchase order associated with the delivered service. The order may be directly opened, or the provider may search all orders to retrieve the correct order. After opening the purchase order, the provider determines if the service purchased matches the service delivered. If the service purchased matches the service delivered, then the provider may proceed to getting paid for the service.

If the service purchased does not match the service delivered, for example if additional services were delivered or if the service purchased was incorrect, then the provider may modify the order to reflect the changes. If the provider determines an inappropriate service was ordered, the provider may make a verbal recommendation to the consumer for the appropriate service, including the specific cost of the service. If the consumer verbally agrees (or otherwise approves the added service), the provider may perform the new service at that time, if it is not substantially different (for example, requiring similar time, equipment, and other resources to the previous, incorrect order). In some examples, the provider may modify the order within 24 hours of performing the service. If the new service is substantially different from the previous order, the provider and consumer may discuss a future appointment.

If the provider determines that an additional service is needed (for example, imaging, lab work, treatment, etc.) at the time of performing the purchased service, the provider may make a verbal recommendation to the consumer for the appropriate service, including the specific cost of the service. If the consumer verbally agrees, the provider may perform the new service at that time, if possible and appropriate. In some examples, the provider may add the additional service to the original order on the e-commerce platform within a specified time after performing the service. If the additional service is performed at a later time and/or by a separate provider, the consumer may purchase the additional service through the e-commerce platform.

Providers would like to simplify their administrative processes, particularly the bill review cycle, and eliminate claims complexity. Providers would like to improve their cash flow and reduce patient receivables. Consumers would also like to eliminate the uncertainty or surprise of unexpected bills associated with services received.

Thus, systems and methods are provided for making bundles of care look like a health care service bundle indicator to consumers, procedure and diagnosis codes to providers, and auto-adjudicated claims to a TPA. The e-commerce platform eliminates the normal processing overhead associated with claims, instead issuing receipt documentation for services rendered. This receipt documentation will be issued to consumers while also being auto-adjudicated by their insurer to apply against their health plan deductible. Consumers will no longer have to receive or reconcile bills from their provider and their health plan's Explanation of Benefits (EOB) statement.

Providers have the freedom to set their own fees and attract insured patients. Money from consumers will be placed into escrow and transfers between an employer account and the e-commerce platform payment processor will be configured before services are rendered, ensuring prompt payment to providers for patient services with no financial risk, reducing their patient receivables and improving their cash flow.

Consumers pay at the point of purchase on the e-commerce platform, and funds are released from the payment processor to a provider once the provider confirms that purchased services were rendered by submitting an invoice, or claim. This eliminates the need for providers to file a claim to a plan administrator and for any surprise bills to consumers. Once this verification takes place, the information will be released to the plan administrator in the form of a claim, or receipt documentation, with a high probability of auto-adjudication. The plan administrator processes the claim and applies it against the consumer's deductible.

FIGS. 7-8 illustrate example methods for a health care billing system. In particular, FIG. 7 shows a high-level flow chart illustrating an example method 700 for a health care billing system in accordance with the prior art, while FIG. 8 shows a high-level flow chart illustrating an example method 800 for a health care billing system in accordance with the current disclosure.

Previous methods, such as method 700 in FIG. 7, begin with providing a health care service to a consumer and billing last. The method 700 is typically carried out by four different entities, including a consumer/patient 702, a provider 704, a billing entity 706, and a health care plan third-party administrator (TPA) 708.

At 710, the consumer 702 goes to a doctor's appointment. At 712, the provider 704 checks in the patient and verifies eligibility and coverage. At 714, the provider 704 provides the care to the consumer 702. At 715, the consumer leaves the office. At 716, the provider 704 updates the electronic medical record (EMR) of the consumer 702 and sends billing information to the billing entity 706. At 718, the billing entity 706 submits a claim to the TPA 708, manually or via a clearinghouse. At 720, the TPA 708 receives the claim. At 722, the TPA 708 adjudicates the claim based on coverage and a negotiated rate. At 724, the TPA 708 sends a settled claim/remittance to the provider 704. Further, at 726, the TPA 708 creates an explanation of benefits (EOB) for the consumer 702. At 730, the provider 704 receives the settled claim and creates an invoice for the consumer 702. At 732, the consumer 702 receives the bill or invoice from the provider 704 or the billing entity 706. At 734, the consumer 702 receives the EOB from the TPA 708. At 736, if the consumer 702 understands that payment is being requested via the invoice or the EOB ("Y"), then the consumer 702 pays the provider 704 at 738. If the consumer 702 does not understand the invoice ("N"), the member does not pay the provider and sits on the invoice at 740. Consequently, the provider 704 sends invoices to the consumer 702 until the consumer pays or the debt goes to collection at 742. At 728, the billing entity 706 may determine if the consumer 702 has paid the invoice, and may continue sending a bill to the consumer 702 ("N") until the consumer pays the invoice ("Y"), at which point the method 700 ends.

In such methods, the provider may not receive payment for a service rendered until the consumer pays the bill, however the consumer may sit on the invoice for an indeterminate amount of time. The consumer receives an Explanation of Benefits, which may confuse the consumer as he or she may not understand why some CPT codes are included in the bill.

In contrast, method 800 in FIG. 8 may be carried out by a consumer 802, a provider 804, a TPA 806, and the e-commerce platform 808. The method 800 begins at 810, wherein the consumer 802 shops on the e-commerce platform 808 for health care services. As described above, the consumer 802 may select a health care service bundle (represented by a health care service bundle indicator) and pay the out-of-pocket cost based on the consumer's health care plan prior to visiting a provider 804. At 812, the consumer 802 visits the provider 804 and receives the purchased service. At 814, the consumer 802 may optionally rate the experience via the e-commerce platform 808.

Meanwhile, at 816 the provider 804 receives the purchased order from the e-commerce platform prior to the consumer 802 visiting the provider 804. After providing the services to the consumer 802, the provider 804 checks out the consumer 802 via the e-commerce platform 808.

Meanwhile, after the consumer 802 places an order on the e-commerce platform at 810, the e-commerce platform receives the order at 820. After the provider 804 checks out the consumer 802 via the e-commerce platform 808 at 818, the e-commerce platform 808 performs several actions. At 822, the e-commerce platform remits payment to the provider for settlement. At 824, the provider 804 accepts the payment via ACH or a merchant account, as non-limiting examples. At 826, the e-commerce platform 808 remits a claim to the TPA 806 for adjudication. At 828, the TPA 806 adjudicates the claim and posts the claim to the patient file. At 830, the e-commerce platform 808 sends, via a secure email as a non-limiting example or via an interface of the e-commerce platform 808 as described above, receipt documentation to the consumer 802. At 832, the consumer 802 receives the receipt documentation from the e-commerce platform 808. As described herein, the receipt documentation describes the purchased service, a cost breakdown of the service, technical and non-technical descriptions of the rendered service, provider information, patient information, and health care plan information.

Thus, the method 800 begins with the consumer paying for a health care service prior to receiving the service. The payment is held in escrow by the e-commerce platform until the provider delivers the service, and the provider receives the payment once the provider checks out the consumer through the e-commerce platform. The e-commerce platform then sends receipt documentation, such as the receipt documentation 672 shown in FIG. 6J, to the consumer. Since the health care consumer ordered and paid for the bundle of health care services prior to visiting a health care provider, there is far less confusion about services rendered and the cost of each service. In this way, the e-commerce platform increases health care transparency and empowers health care consumers, while reducing overhead for health care providers.

Consumers might need guidance when purchasing health care services. As first time shoppers in health care, they will want to know which types of services are often purchased together and what kind of modifications to their purchase might take place at the provider's office. They will need clarity that they are purchasing the right services at the right time. Thus, systems and methods are provided for the generation of a personalization engine. Similar to the e-commerce shopping sites consumers already use for products, consumers will receive recommendations for services based on their past purchases and the purchases of other consumers. Consumers will be able to see which health care service bundle indicators are commonly purchased together, and what modifications and add-ons might take place at the point of service.

FIG. 9 illustrates an example method 900 for personalizing an e-commerce health care platform for a health care consumer. Method 900 relates to a personalization engine 920 that analyzes services rendered and tracks consumer usage. Such a personalization engine 920 is key to consumer engagement and increased "stickiness" over time. The basis of the personalization engine is observing consumer behavior. Purchasing habits of consumers are recorded and categorized by multiple factors including age, sex, geography, and so on, for example input of other users 904 may be recorded in a user profile database 914. A personalization database 910 may include the user profile database 914 in addition to a user profile database 912 which records input from the user 902, a provider attributes database 916 which records input from the provider 906, and a curated SKU database 918 which records system parameters 908. For example, the curated SKU database 918 may comprise a plurality of health care service bundle indicators as discussed herein. At a first encounter, consumers will receive recommendations based on a curated database of nationally purchased services. Over time, the personalization engine 920 will make personalized recommendations 926 based on recorded consumer behavior. To that end, the personalization engine 920 may include a master attribute table 922 and an adjacency engine 924, which retrieve information from the personalization database 910 and process the retrieved information to generate a personalized recommendation 926. The personalized recommendation 926 may be input to the user profile 912.

Several embodiments for an e-commerce marketplace have been described herein above. In one embodiment, a method comprises, responsive to a query from a user via a user device, retrieving from a database a list of responses comprising one or more health care providers offering one or more health care services at a provider-supplied price; filtering the list of responses based on a geographic location included in the query; providing, for display on the user device, the filtered list of responses; receiving a payment from the user for a response selected from the filtered list of responses; automatically sending a notification of the payment to a provider associated with the selected response; and responsive to receiving an order fulfillment notification from the provider, automatically providing the payment to the provider. In some examples, the provider-supplied price may be adjusted by a provider at any time.

As one example, the method further comprises providing, for display on the user device, an out-of-pocket cost for each response of the list of responses. For example, the payment equals the out-of-pocket cost for the selected response.

As another example, the method further comprises automatically sending a health care claim to a health insurance administrator responsive to receiving the order fulfillment notification from the provider. In another example, the method further comprises automatically sending the health care claim to the user in a user-oriented format different than a format of the health care claim sent to the health insurance administrator.

As another example, the one or more services are represented by a health care bundle indicator, the health care bundle indicator configured to uniquely identify the one or more services, the provider, and a location of the provider. In one example, the provider-supplied price is associated with the health care bundle indicator. As an example, the health care bundle indicator comprises a sequence of alphanumerical characters.

In another embodiment, a computer-readable storage medium including an executable program stored thereon, the program configured to cause a computer processor to: retrieve health care claims data from one or more databases; process the health care claims data to identify a combination of current procedural terminology (CPT) codes provided to a plurality of patients in a single health care interaction; assemble the combination of CPT codes into a bundle of health care services; generate a product code for a bundle of health care services; receive a price for the product code from a health care provider; generate a health care service bundle indicator for the health care provider based on the product code; and assign the price to the health care service bundle indicator.

In one example, generating the product code is based on one or more of a health care category, a health care service group, and a set of health care procedures (e.g., the combination of CPT codes) for the bundle of health care services.

As another example, generating the health care service bundle indicator comprises concatenating the product code to unit codes associated with the health care provider. As yet another example, generating the health care service bundle indicator further comprises concatenating the concatenated product code and unit codes associated with the health care provider with a sequence of alphanumeric characters identifying a location of the health care provider. In further examples, the unit codes associated with the health care provider identify an applicable provider network of the health care provider.

In yet another embodiment, an apparatus facilitating a health care marketplace comprises a processor and memory storing processor-executable instructions that cause the processor to: receive, from a user, a payment for a bundle of health care services provided by a health care provider prior to the user visiting the health care provider; automatically generate receipt documentation responsive to receiving an order fulfillment notification from a health care provider indicating that the user received the bundle of health care services from the health care provider, wherein the receipt documentation includes one or more current procedural terminology (CPT) codes associated with the bundle of health care services; send, to the user, the receipt documentation formatted for display to the user and including a non-technical description of the one or more CPT codes; and send, to an insurance administrator for a health insurance plan of the user, the receipt documentation formatted as a health care claim.

In one example, the receipt documentation includes a list of CPT codes associated with the bundle of health care services and the payment received.

In another example, the order fulfillment notification includes information regarding additional services provided by the health care provider to the user not included in the receipt documentation sent to the user, and wherein the receipt documentation sent to the insurance administrator includes the information regarding the additional services.

In another example, the memory is further storing processor-executable instructions that cause the processor to, responsive to receiving the information regarding the additional services, calculate an additional payment from a user based on the information regarding the additional services, and request the additional payment from the user. As an example, the additional payment is calculated based on a health insurance benefits plan of the user.

In another example, the payment for the bundle of health care services comprises an out-of-pocket cost to the user based on a health insurance benefits plan of the user.

In another example, the receipt documentation further includes one or more diagnostic codes, information identifying the user, information identifying the health care provider, information regarding the payment, and a cost breakdown indicating an out-of-pocket cost to the user for the bundle of health care services and an amount covered by the health insurance plan of the user.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a computing system, comprising:
providing, for a consumer, remote access to the computing system over a network via a consumer computing device communicably coupled to the network, wherein the computing system comprises a data-holding subsystem and a logic subsystem, the data-holding subsystem storing machine readable instructions executable by the logic subsystem;
providing, for a provider, remote access to the computing system over the network via a provider computing device communicably coupled to the network; and
executing the machine readable instructions at the logic subsystem to:
receive national claims information from a first non-transitory storage device included in the data-holding subsystem;
receive metadata comprising order information, provider listings, order fulfillment data, and medical classification data from a second non-transitory storage device included in the data-holding subsystem;
identify one or more current procedural terminology (CPT) codes commonly added to health care services together based on the national claims information and the metadata;
generate a standardized health care service bundle identifier based on the one or more identified CPT codes and an identifier taxonomy;
display, at the consumer computing device, each of the standardized health care service bundle identifier and a price for the standardized health care service bundle identifier;
receive, from the consumer computing device, a prepayment for the standardized health care service bundle identifier, wherein the prepayment is received prior to a particular health care service being provided;
place the prepayment into escrow; and
responsive to receiving an order fulfillment notification from the provider computing device, wherein the order fulfillment notification indicates that the particular health care service has been provided,
automatically transfer the prepayment from escrow to the provider computing device, automatically generate a health care claim in a first format based on the particular health care service, consumer information from the consumer computing device, and provider information from the provider computing device;

automatically send the health care claim in the first format to the consumer computing device;

automatically generate the health care claim in a second format, the second format different from the first format, based on the particular health care service, the consumer information from the consumer computing device, and the provider information from the provider computing device; and automatically send the health care claim in the second format to a health insurance administrator computing device.

2. The method of claim 1, wherein the health insurance administrator computing device is communicably coupled to the network and provides remote access for a health insurance administrator to the computing system over the network.

3. The method of claim 1, wherein the machine readable instructions are further executed at the logic subsystem to:

display, at the provider computing device, the standardized health care service bundle identifier; and receive, from the provider computing device, the price for the standardized health care service bundle identifier.

4. The method of claim 1, wherein the identifier taxonomy comprises a health care service category, a health care service group, a health care service type, a location, and a single unit code, the health care service group corresponding to a first subset of health care services within the health care service category and the health care service type corresponding to a second subset of health care services within the health care service group.

5. The method of claim 4, wherein the location corresponds to a geographical region, or wherein the location corresponds to a specific health care practice and the single unit code corresponds to a specific provider at the specific health care practice.

6. The method of claim 1, wherein the machine readable instructions are further executed at the logic subsystem to assemble the one or more identified CPT codes into a bundle of health care services, the standardized health care service bundle identifier representing the bundle of health care services.

7. The method of claim 6, wherein the bundle of health care services comprises one or more first CPT codes corresponding to a standard service and one or more second CPT codes corresponding to one or more additional services selected by the provider via the provider computing device and/or the consumer via the consumer computing device, or selected based on the identifier taxonomy.

8. A method for a computing system, comprising:

providing, for a consumer, remote access to the computing system over a network via a consumer computing device communicably coupled to the network, wherein the computing system comprises a data-holding subsystem and a logic subsystem, the data-holding subsystem storing machine readable instructions executable by the logic subsystem;

providing, for a provider, remote access to the computing system over the network via a provider computing device communicably coupled to the network; and executing the machine readable instructions at the logic subsystem to:

receive a prepayment for a standardized health care service bundle identifier from the consumer computing device before a particular health care service is provided, the standardized health care service bundle identifier generated based on one or more current procedural terminology (CPT) codes and displayed at the consumer computing device;

place the prepayment into escrow;

automatically transfer the prepayment from escrow to the provider computing device upon receiving an order fulfillment notification from the provider computing device;

automatically generate a health care claim in a first format based on the particular health care service, consumer information from the consumer computing device, and provider information from the provider computing device, and send the health care claim in the first format to the consumer computing device; and automatically generate the health care claim in a second format based on the particular health care service, the consumer information from the consumer computing device, and the provider information from the provider computing device, and send the health care claim in the second format to a health insurance administrator computing device communicably coupled to the network.

9. The method of claim 8, wherein the standardized health care service bundle identifier is further generated based on an identifier taxonomy, and wherein the one or more CPT codes are identified based on national claims information received from a first non-transitory device included in the data-holding subsystem and metadata comprising order information, provider listings, order fulfillment data, and medical classification data received from a second non-transitory storage device included in the data-holding subsystem.

10. The method of claim 8, wherein a price for the standardized health care service bundle identifier is displayed at the consumer computing device with the standardized health care service bundle identifier.

11. The method of claim 8, wherein the health care claim in the first format is receipt documentation formatted for display to the consumer.

12. The method of claim 8, wherein the health care claim in the first format includes a non-technical description of the one or more CPT codes.

13. The method of claim 8, wherein the health care claim in the second format includes a technical description of provided services in a standardized format.

14. The method of claim 8, wherein the health care claim in the second format includes the one or more CPT codes, medical classifications, insurance information of the consumer, and the provider information.

* * * * *